United States Patent
Kumar et al.

(10) Patent No.: US 9,977,033 B2
(45) Date of Patent: May 22, 2018

(54) METHODS FOR ASSESSING CANCER RECURRENCE

(71) Applicants: Addanki Pratap Kumar, San Antonio, TX (US); Izhar Singh Batth, San Antonio, TX (US); Rita Ghosh, San Antonio, TX (US); Roble Bedolla, San Antonio, TX (US); Ian M. Thompson, Jr., San Antonio, TX (US)

(72) Inventors: Addanki Pratap Kumar, San Antonio, TX (US); Izhar Singh Batth, San Antonio, TX (US); Rita Ghosh, San Antonio, TX (US); Roble Bedolla, San Antonio, TX (US); Ian M. Thompson, Jr., San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days. days.

(21) Appl. No.: 14/024,348

(22) Filed: Sep. 11, 2013

(65) Prior Publication Data
US 2014/0105933 A1    Apr. 17, 2014

Related U.S. Application Data

(60) Provisional application No. 61/699,834, filed on Sep. 11, 2012.

(51) Int. Cl.
| | | |
|---|---|---|
| *G01N 33/50* | (2006.01) | |
| *G01N 33/574* | (2006.01) | |
| *A61K 31/58* | (2006.01) | |
| *A61K 39/00* | (2006.01) | |
| *G01N 33/68* | (2006.01) | |
| *A61K 31/337* | (2006.01) | |
| *A61K 31/573* | (2006.01) | |
| *A61K 31/137* | (2006.01) | |

(52) U.S. Cl.
CPC ....... *G01N 33/6893* (2013.01); *A61K 31/137* (2013.01); *A61K 31/337* (2013.01); *A61K 31/573* (2013.01); *A61K 31/58* (2013.01); *A61K 39/0011* (2013.01); *G01N 33/57434* (2013.01); *G01N 2333/4706* (2013.01); *G01N 2800/54* (2013.01)

(58) Field of Classification Search
None
See application file for complete search history.

(56) References Cited

U.S. PATENT DOCUMENTS

| | | |
|---|---|---|
| 6,090,559 A | 7/2000 | Russell et al. |
| 7,332,290 B2 | 2/2008 | Rubin et al. |
| 7,579,152 B2 | 8/2009 | Yeh |
| 7,592,145 B2 | 9/2009 | Bao et al. |
| 7,611,845 B2 | 11/2009 | Taneja et al. |
| 7,666,595 B2 | 2/2010 | Rubin et al. |
| 7,803,552 B2 | 9/2010 | Rubin et al. |
| 7,807,393 B2 | 10/2010 | Thaxton et al. |
| 7,914,988 B1 | 3/2011 | Chudin et al. |
| 7,993,830 B2 | 8/2011 | An et al. |
| 8,110,363 B2 | 2/2012 | Chudin et al. |
| 8,148,093 B2 | 4/2012 | Simon et al. |
| 8,192,931 B2 | 6/2012 | Fradet et al. |
| 2003/0073674 A1* | 4/2003 | Slaga et al. .................. 514/171 |
| 2003/0228639 A1* | 12/2003 | Wright et al. ............... 435/7.23 |
| 2008/0171051 A1* | 7/2008 | Johnston et al. .......... 424/155.1 |
| 2009/0181384 A1* | 7/2009 | Nekarda ............... C12Q 1/6886 435/6.14 |
| 2009/0326051 A1* | 12/2009 | Corey ................... C12N 15/111 514/44 R |
| 2011/0020230 A1 | 1/2011 | Thaxton et al. |
| 2011/0230361 A1 | 9/2011 | Moreno et al. |
| 2012/0108453 A1 | 5/2012 | Smit et al. |

OTHER PUBLICATIONS

Ganapathy et al. (Clinical Cancer Research, 2009, 15:1601-1611).*
O'Toole et al. (Cancer Research, 2006, 66:9162-9170).*
Ponten et al. (Molecular Systems Biology, 2009, 5:1-9 and A-P).*
Etzioni et al. (Nature Review, 2003, 3:1-10).*
Mercer (Immunodiagnosis of Cancer, 1990, pp. 39-54).*

* cited by examiner

*Primary Examiner* — Julie Wu
(74) *Attorney, Agent, or Firm* — Norton Rose Fulbright US LLP

(57) ABSTRACT

Certain embodiments are directed to methods of identifying a subject having a higher risk of prostate cancer recurrence. The methods can include the step of measuring levels of one or more of FLIP, transcription factor Sp1, and transcription factor Sp3 in a prostate sample from the subject, wherein elevated levels of FLIP, transcription factor Sp1, and transcription factor Sp3 identify a subject as high risk for prostate cancer recurrence.

9 Claims, 21 Drawing Sheets

Sp1 0.66

FLIP 0.71

Gleason 0.76

AUC .93

Sensitivity 80.0% Specificity 85.3%

Correctly Classified 83%

METHODS FOR ASSESSING CANCER RECURRENCE

PRIORITY CLAIM

This application claims priority to U.S. provisional application 61/699,834 filed Sep. 11, 2012, which is incorporated herein by reference in its entirety.

STATEMENT REGARDING FEDERALLY FUNDED RESEARCH

This invention was made with government support under grant number CA135451 awarded by the National Institutes of Health. The government has certain rights in the invention.

BACKGROUND

Prostate cancer (PCA) is the second leading cause of cancer-related death in men and is expected to cause 28,170 deaths in the United States in 2012 (Siegel et al. (2012) *CA Cancer J Clin* 62: 10-29). PCA generally affects men over 65 years of age but remains indolent and asymptomatic in a majority of cases. The histopathological and molecular heterogeneity of the disease makes prediction of prognosis challenging. Although PSA is the most widely used serum marker for prostate cancer, it has no accepted cut-off point with high sensitivity and specificity and often leads to false positive results (Manne et al. (2005) *Drug Discov Today* 10: 965-976; Grizzle et al. (2004) *Urol Oncol* 22: 337-343; Thompson et al. (2005) *JAMA* 294: 66-70). Furthermore, there are currently no molecular markers that can be used to reliably predict which premalignant lesions will recur or develop into invasive PCA (Manne et al. (2005) *Drug Discov Today* 10: 965-976; Grizzle et al. (2004) *Urol Oncol* 22: 337-343; Thompson et al. (2005) *JAMA* 294: 66-70; Salagierski and Schalken (2012) *J Urol* 187: 795-801; Kristiansen (2012) *Histopathology* 60: 125-141). A valid biomarker should have the following characteristics: (i) accuracy (should not falsely predict positive or negative results); (ii) selectivity (ability to diagnose the disease during disease progression); and (iii) specificity (ability to distinguish cancerous from non-cancerous phenotype). Although PSA fulfills most of these criteria and is widely used, it is limited by its low values of specificity and selectivity (Manne et al. (2005) *Drug Discov Today* 10: 965-976; Grizzle et al. (2004) *Urol Oncol* 22: 337-343; Thompson et al. (2005) *JAMA* 294: 66-70; Salagierski and Schalken (2012) J Urol 187: 795-801; Kristiansen (2012) *Histopathology* 60: 125-141).

Because of the growing evidence for over-treatment of prostate cancer, it is important to identify and validate new prognostic markers that will predict clinically significant prostate cancer (Kristiansen (2012) *Histopathology* 60:125-141; Lopergolo and Zaffaroni (2009) *Cancer* 115:3058-3067; Lughezzani et al. (2010) *Eur Urol* 58:687-700; Fromont et al. (2012) *Prostate*; Garcia et al. (2006) *Clin Cancer Res* 12:980-988). Such markers will enable the targeted treatment of patients with aggressive tumors while avoiding unnecessary treatment and its side effects in patients with indolent disease.

SUMMARY

Certain embodiments are directed to methods of detecting and/or classifying cancer in a subject comprising measuring levels of biomarkers that are indicative of cancer recurrence. In certain aspects the methods are directed to identifying aggressive tumors, i.e., those tumors that grow quickly and tending to spread rapidly. These aggressive tumors result in a poor prognosis. A poor prognosis means that there is a higher probability of cancer recurrence after a patient receives a treatment, or a shortened period between patient treatment and the time the patient presents with a recurrence of the cancer. The levels of biomarkers can be measured at the nucleic acid or protein level. In certain aspects, a biomarker is measured by contacting a biological sample with a binding agent that binds a biomarker such as FLIP, Sp transcription factor (e.g., transcription factor Sp1, transcription factor Sp3, and the like) and/or RON tyrosine kinase to form a complex of a binding agent and at least one of FLIP, Sp transcription factor (e.g., transcription factor Sp1, transcription factor Sp3, and the like) and/or RON tyrosine kinase; detecting the complex; and quantifying the detected complex to measure the amount of target protein in the sample. In certain aspects, the Sp transcription factor is transcription factor Sp1 and/or transcription factor Sp3. In certain aspects, an elevated level of the biomarker identifies or detects the presence of cancer; classifies or stratifies the cancer type or grade; or provides a prognosis (likelihood or probability of recurrence). The term "elevated level" as used herein with respect to the level of a biomarker is a level that is above a reference level. A reference level can be a median or average level of a biomarker in samples from subjects not having cancer, or subjects having had a non-recurrent cancer, or subjects having a distinct form or grade of cancer. A reference can be a predetermined level and need not be determined simultaneously. Elevated levels can be any level provided that the level is greater than a corresponding reference level. For example, an elevated level of a particular protein can be 0.5, 1, 2, 3, 4, 5, 6, 7, 8, 9, 10, or more fold greater than a reference level. In certain aspects, a level is determined to be above a reference level by statistical methods known in the art.

Levels of biomarkers can be used to classify a cancer. In certain aspects, a cancer can be classified relative to aggressiveness, prognosis, or grade. In other aspects, levels of biomarkers classify the cancer relative to risk of recurrence. In still further aspects, a biomarker can be used to provide a diagnosis or prognosis. In certain aspects, biomarker levels can be used in determining which treatments should or should not be administered to a subject. In certain aspects an aggressive tumor or a patient having a poor prognosis is treated more aggressively. In a further aspect an indolent tumor or a patient having a good prognosis can be spared treatments that may unduly harm the patient.

The biological sample can be a tissue biopsy, urine, or blood. In certain aspects, the biological sample is a tissue biopsy.

A majority of cancers including lung, skin, and pancreatic cancers express elevated levels of Sp1 and FLIP. However, their importance in predicting recurring cancer is not known. The current methods can be applied to any cancer that expresses higher levels of these proteins. In certain aspects the cancer is prostate cancer. In certain aspects the methods are directed to measuring prostate cancer biomarker levels as described herein in conjunction with a Gleason score. In still a further aspect FLIP and Sp transcription factor levels are assessed in conjunction with RON tyrosine kinase levels. In one aspect elevated levels of RON are indicative of an aggressive form of cancer. In other aspects elevated levels of nuclear localized RON is indicative of an aggressive form of cancer.

In certain aspects the biomarker-binding agent is immobilized on a support. The binding agent can be an antibody, such as a monoclonal or polyclonal antibody that binds a biomarker. In a further embodiment the binding agent can be a nucleic acid that specifically binds a nucleic acid encoding a biomarker. The method can further comprise linking or incorporating a label to the binding agent, the biomarker, target nucleic acid, the binding agent and the biomarker, or the binding agent and the target nucleic acid.

In certain aspects, biomarker levels are measured by detecting the level of protein in a sample or the level of a nucleic acid encoding the biomarker that is indicative of the target protein levels in a sample. Detection methods can include but are not limited to the detection of proteins or nucleic acids. In certain aspects, immunoassays such as ELISA or immunohistochemistry are used to detect and/or measure target proteins. In a further aspect, PCR or nucleic acid hybridization can be used to detect and/or measure target nucleic acids.

In certain aspects, a sample is taken from a subject (e.g., a patient) and analyzed at several time points as part of monitoring the subject before, during, and/or after the treatment of the cancer (e.g., surgical or pharmaceutical treatment).

In certain aspects, the subject has been diagnosed with cancer. In a further aspect, the subject and/or the subject's cancer has been assessed and classified using standard classification methodology. In certain aspects, the subject's cancer has been classified using the Gleason grading system. The classification of a subject's cancer can be used in determining at least one or more of (a) the risk of cancer recurrence, or (b) the aggressiveness of therapies or secondary therapies to be administered to the subject.

Certain embodiments are directed to methods of identifying a subject having a higher risk of prostate cancer recurrence. The methods include the step of measuring levels of one or more of FLIP, Sp transcription factor (e.g., transcription factor Sp1, transcription factor Sp3, and the like) and/or RON tyrosine kinase in a prostate sample from the subject, wherein levels of one or more of FLIP, Sp transcription factor (e.g., transcription factor Sp1, transcription factor Sp3, and the like) and/or RON tyrosine kinase are determined to be elevated. In certain aspects, elevated levels of one or more of FLIP, Sp transcription factor (e.g., transcription factor Sp1, transcription factor Sp3, and the like) and/or RON tyrosine kinase identify a subject as high risk, having an increased likelihood, or an increased probability for prostate cancer recurrence.

In certain aspects, levels of FLIP, Sp transcription factor (e.g., transcription factor Sp1, transcription factor Sp3, and the like) and/or RON tyrosine kinase are determined by measuring protein levels of FLIP, Sp transcription factor (e.g., transcription factor Sp1, transcription factor Sp3, and the like) and/or RON tyrosine kinase.

In other aspects, levels of FLIP, Sp transcription factor (e.g., transcription factor Sp1, transcription factor Sp3, and the like) and/or RON tyrosine kinase are determined by measuring mRNA levels of FLIP, Sp transcription factor (e.g., transcription factor Sp1, transcription factor Sp3, and the like) and/or RON tyrosine kinase.

In certain aspect, a prostate cancer sample can be a biopsy or resected tissue.

Moieties of the invention, such as polypeptides, peptides, oligonucleotides, or nucleic acids, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation."

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
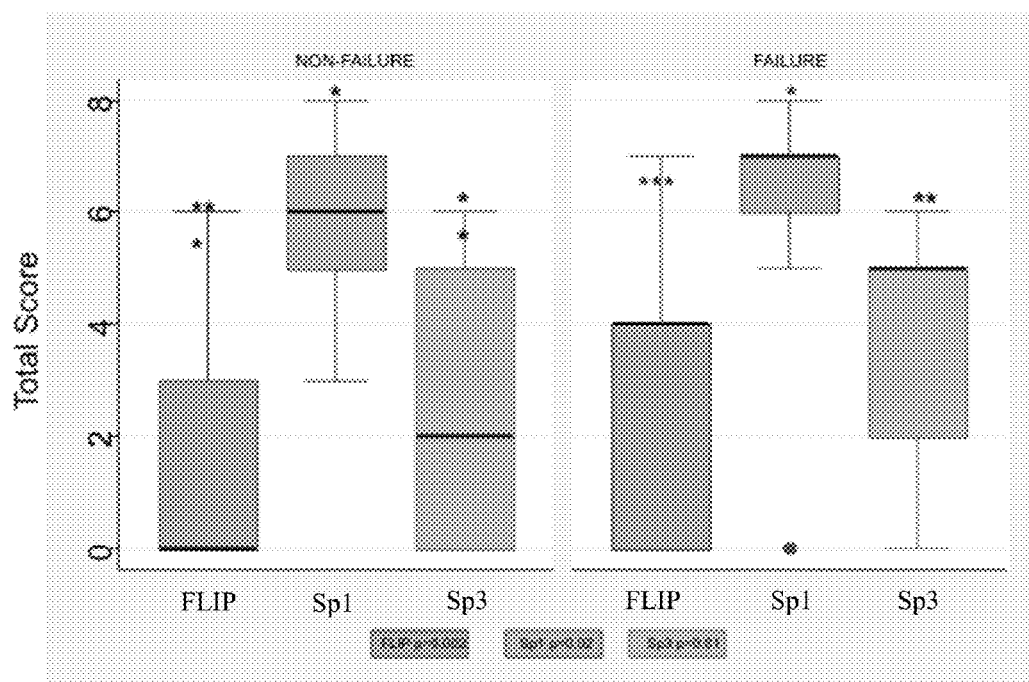
FIG. 1. Box plots showing significant differences in mean total score for IHC of Sp1, Sp3, and FLIP between recurrent and non-recurrent cases as determined by Wilcoxon rank-sum test.

Research over the past decade has identified a number of biomarkers that are associated with high Gleason grade disease (Lopergolo and Zaffaroni (2009) *Cancer* 115:3058-3067; Lughezzani et al. (2010) *Eur Urol* 58:687-700; Fromont et al. (2012) *Prostate*; Garcia et al. (2006) *Clin Cancer Res* 12: 980-988; Kumar et al. (2007) *Clin Cancer Res* 13:2784-2794; Ghosh et al. (2007) *Neoplasia* 9:893-899; Ganapathy et al. (2009) *Clin Cancer Res* 15:1601-1611). Previous studies from the inventors' laboratory found a correlation between expression of FLICE-inhibitory protein (FLIP) and tumor grade in human prostate cancer (Ganapathy et al. (2009) *Clin Cancer Res* 15: 1601-1611). Specifically, the inventors found that high-grade Gleason tumors show increased FLIP staining compared with low-grade Gleason tumors (p=0.04) (Ganapathy et al. (2009) *Clin Cancer Res* 15:1601-1611). In experiments to understand the role of FLIP regulation during prostate carcinogenesis, the inventors identified transcription factors Sp1 and Sp3 as important regulators of FLIP transcriptional activity in prostate cancer cells (Ganapathy et al. (2009) *Clin Cancer Res* 15:1601-1611). The inventors further demonstrated that Sp1 trans-activates the FLIP promoter while Sp3 inhibits Sp1-mediated trans-activation, thus implicating a role for these factors during prostate carcinogenesis. However, it was not known whether any of these markers could achieve the sensitivity and specificity necessary to distinguish aggressive from indolent disease. The inventors evaluated whether the "biomarker signature" of FLIP, Sp1, and Sp3 can predict the development of prostate cancer recurrence by immunohistochemical evaluation of tissue samples obtained from patients who underwent prostatectomy as primary treatment for prostate cancer and were observed for at least 5 years with PSA measurements. The inventors show that the combination of FLIP, Sp1, Sp3, and Gleason score is an excellent predictor of biochemical recurrence. The area under the receiver operator characteristic curve for FLIP, Sp1, and Sp3 when predicting PSA failure was 0.71, 0.66, and 0.68 respectively; however, when these three markers were combined with Gleason score the AUC increased to 0.93. This level of prediction for PSA failure suggests that this biomarker panel is an important predictor of biochemical recurrence.

Effective clinical management of prostate cancer (PCA) has been hampered by significant intratumoral heterogeneity combined with an incomplete understanding of the molecular events associated with the development of the disease and subsequent recurrence following traditional treatments (Yap et al. (2011) *Nat Rev Clin Oncol* 8:597-610; Petrylak et al. (2004) *N Engl J Med* 351:1513-1520). Given the individual genetic variation and the heterogeneity of the disease, personalized treatment approaches are needed for successful management of PCA. To develop such individualized treatment approaches biomarkers or a "biomarker signature" need to be identified that can be used to stratify patients according to response to specific treatments (Armstrong et al. (2012) *Eur Urol* 61:549-559; Shariat et al. (2011) *Arch Esp Urol* 64:681-694). Although serum-based PSA screening is widely used, PSA has the following limitations as an early detection biomarker (Armstrong et al. (2012) *Eur Urol* 61:549-559; Shariat et al. (2011) *Arch Esp Urol* 64:681-694; Andriole et al. (2012) *J Natl Cancer Inst* 104:125-132; Payton (2012) *Nat Rev Urol* 9:59): (i) Elevated levels of serum PSA have been observed not only in prostate cancer, but also in benign prostatic hyperplasia patients, therefore PSA is not specific to prostate cancer, and (ii) PSA is not sufficiently sensitive as indicated by the Prostate Cancer Prevention Trial (PCPT), which demonstrated that 15% of men with PSA levels of 4 ng/ml had prostate cancer and 15% of these patients had high Gleason grade disease. In addition, two randomized trials showed a modest effect of PSA screening on prostate cancer mortality, suggesting a substantial risk of negative biopsy and over-diagnosis and over-treatment of indolent cancer. Although numerous markers including α-methyacylCoA-racemase (AMCAR), fatty acid synthetase (FASN), ERG, and prostate-specific membrane antigen (PSMA), have been identified based on preclinical studies and shown to be associated with the outcome of prostate cancer after surgical treatment using human tissue samples, very few of these have predictive value independent of traditional prognostic factors such as Gleason score, pathological stage, and pretreatment PSA levels (Salagierski and Schalken (2012) *J Urol* 187:795-801; Kristiansen (2012) *Histopathology* 60:125-141).

The inventors have assessed the expression of the anti-apoptotic protein FLIP and the transcription factors Sp1 and Sp3 by immunohistochemical evaluation of tissue samples obtained from 64 patients who underwent radical prostatectomy as primary treatment for prostate cancer. The inventors believe that this is the first report of FLIP, Sp1, and Sp3 expression and the correlation among these proteins in biochemically recurrent PCA samples. Although increased expression of Sp1, Sp3, or FLIP showed significant differences between PSA failure and non-failure cases, individually they are not strong predictors of poor clinical outcome based on AUC when PSA failure is used as a surrogate outcome: the area under the ROC curve for FLIP, Sp1, Sp3, and Gleason as a predictor of PSA failure and non-failure cases was 0.71, 0.66, 0.68, and 0.76 respectively. On the other hand, the biomarker signature of Sp1/Sp3/FLIP combined with Gleason achieved an AUC of 0.93. These data indicate excellent discrimination between PSA failure and non-failure cases and suggest that this biomarker signature is an important predictor of the probability of recurrence. This is significant since current diagnostic procedures cannot distinguish between aggressive and clinically indolent disease, resulting in more men being treated for the disease than necessary. The three-gene signature combined with Gleason grade was accurate 83% of the time in our cohort.

The observation that Sp1/Sp3 and FLIP are predictors of clinical outcome reflect their role in cancer, particularly prostate cancer. Increased levels of Sp1/Sp3/FLIP might be (and not to be held to any particular mechanism) related to apoptotic resistance and progression to recurrence or progression from low- to high-risk prostate cancer. Cellular FLICE-inhibitory protein (c-FLIP) is a truncated form of caspase-8 that has been shown to play a critical role in the development of resistance to therapeutics in cancer cells by inhibiting apoptosis mediated by death receptor signaling (Irmler et al. (1997) *Nature* 388:190-195; Golks et al. (2005) *J Biol Chem* 280:14507-14513). Accordingly, FLIP is overexpressed in various cancers and this overexpression has been shown to determine therapeutic resistance (Rippo et al. (2004) *Oncogene* 23:7753-7760; Mathas et al. (2004) *J Exp Med* 199:1041-1052; Rogers et al. (2007) *Mol Cancer Ther* 6:1544-1551; Ullenhag et al. (2007) *Clin Cancer Res* 13:5070-5075; Korkolopoulou et al. (2007) *Histopathology* 51:150-156; Bullani et al. (2001) *J Invest Dermatol* 117: 360-364; Thomas et al. (2002) *Am J Pathol* 160:1521-1528; Benesch et al. (2003) *Leukemia* 17:2460-2466; Korkolopoulou et al. (2004) *Urology* 63:1198-1204; Lee et al. (2003) *APMIS* 111:309-314). In addition, overexpression of FLIP has been correlated with poor prognosis in colon, bladder, and urothelial cancers (Rippo et al. (2004) *Oncogene* 23: 7753-7760; Mathas et al. (2004) *J Exp Med* 199: 1041-1052; Rogers et al. (2007) *Mol Cancer Ther* 6: 1544-1551; Ullenhag et al. (2007) *Clin Cancer Res* 13: 5070-5075; Korkolopoulou et al. (2007) *Histopathology* 51: 150-156; Bullani et al. (2001) *J Invest Dermatol* 117: 360-364; Thomas et al. (2002) *Am J Pathol* 160: 1521-1528; Benesch et al. (2003) *Leukemia* 17: 2460-2466; Korkolopoulou et al. (2004) *Urology* 63: 1198-1204; Lee et al. (2003) *APMIS* 111: 309-314). Recent studies from the inventors' laboratory demonstrated that specimens from high-grade prostate cancer exhibit higher expression of FLIP than those from low-grade tumors (Ganapathy et al. (2009) *Clin Cancer Res* 15:1601-1611). Furthermore, the inventors also showed that FLIP is regulated transcriptionally through modulation of the transcription factors Sp1 and Sp3 and that inhibition of FLIP prevented prostate tumor development in a preclinical animal model (Ganapathy et al. (2009) *Clin Cancer Res* 15:1601-1611).

Sp1 and Sp3 belong to the Zn-finger family of transcription factors that have been shown to regulate expression of genes involved in various cellular processes of oncogenesis including differentiation, apoptosis, cell migration, and cell cycle progression (Essafi-Benkhadir et al. (2009) *PLoS One* 4:e4478; Kennett et al. (1997) *Nucleic Acids Res* 25:3110-3117; Li and Davie (2010) *Ann Anat* 192:275-283). Sp1 and Sp3 have similar structural features including a highly conserved DNA binding domain and consequently bind to DNA with similar affinity. Although Sp1 is a known trans-activator, Sp3 functions both as an activator and as a repressor depending on the cellular context. Although studies on Sp3 and cancer are lacking, Sp1 levels have been shown to be elevated in a wide variety of cancers including breast, thyroid, hepatocellular, pancreatic, colorectal, gastric, and lung cancer (Li and Davie (2010) *Ann Anat* 192:275-283). Furthermore, abnormal Sp1 protein levels have been correlated with cancer stage and poor prognosis. Accordingly, inhibition of Sp1 or its knock-down to normal cellular levels usually decreases tumor formation, growth, and metastasis. It is noteworthy that the inventors previously showed that Sp1 trans-activates FLIP in prostate cancer cells, whereas Sp3 inhibits this trans-activation (Ganapathy et al. (2009) *Clin Cancer Res* 15:1601-1611). Based on these data the inventors expected to see an inverse association between Sp1 and Sp3 in these samples. However, the observed positive association suggests that Sp1 and Sp3 have a similar functional role in the context of the tumor microenvironment although other factors, such as the small sample size, could also contribute to these observations. Data suggest that FLIP expression can be positively regulated by Sp1 in tumor cells and that targeting Sp1/Sp3/FLIP can be a potential avenue for clinical management of recurring prostate cancer.

The three-gene signature described herein can be used to assess whether a patient's cancer will recur following a given therapy. Such a tool would have a significant impact on the clinical management of prostate cancer. Previous studies reported that AR and pAkt staining predicts recurrence after prostatectomy (Kreisberg et al. (2004) *Cancer Res* 64:5232-5236; Li et al. (2004) *Am J Surg Pathol* 28:928-934) and it is possible that combining these markers with those of this study may further enhance prediction of recurrence. In summary, the data indicate that the Sp1/Sp3/FLIP signature in combination with Gleason grade is predictive of recurrence of prostate cancer and that its clinical application might avoid unnecessary aggressive interventions, thus improving quality of life and reducing healthcare related expenses.

I. BIOMARKERS

The target proteins described herein are used as biomarkers. A biomarker is an organic biomolecule that is differentially present in a sample taken from a subject of one phenotypic status (e.g., having a disease) as compared with another phenotypic status (e.g., not having the disease or having a lesser type of disease). In one aspect, a biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics), of drug toxicity, etc.

In certain aspects, the methods described herein identify subjects having a higher risk of cancer recurrence or differentiate a low risk cancer or hyperplastic condition from a cancerous condition or high risk cancer based on multiple factors including one or more of clinical features, biochemical assays, and gene expression profiling. Biomarkers include proteins, peptides, nucleic acids, or metabolites whose measurement alone (or in a combination) would reliably indicate disease outcome.

Certain embodiments use various biomarkers for assessing a cancer patient. These biomarkers include, but are not limited to FLIP, transcription factor Sp1, and transcription factor Sp3. In certain aspects RON is used in combination with 1, 2, or 3 of these biomarkers to further enhance the reliability of the method. These biomarkers can be used in conjunction with standard clinical assessments, such as Gleason grade.

FLICE-Inhibitory Protein (FLIP).

FLIP was originally identified as a virus-encoded apoptosis-inhibitory protein, but its cellular homologue (c-FLIP) also has the capacity to interfere with formation of the death-inducing signaling complex (DISC) and has a key role in the regulation of GC B cell apoptosis. DISC is formed when Fas-associated death domain (DD)-containing protein (FADD) is recruited to the cell membrane after Fas clustering, which in turn recruits the proenzymatic form of caspase-8/FADD-like IL-1β-converting enzyme (FLICE). Alternative splicing generates two isoforms of cFLIP: a long form (c-FLIPL), which contains a caspase-like domain but is devoid of caspase catalytic activity, and a short form (c-FLIPS) lacking the caspase-like domain. Examples of various isoforms of FLIP are provided in GenBank under accession numbers NP_001120655.1 (GI:187608577), NP_001189445.1 (GI:321267567), NP_001120656.1 (GI: 187608585), NP_001189444.1 (GI:321267564), NP_001189446.1 (GI: 321267569), and NP_001189448.1 (GI: 321267573), each of which is incorporated herein by reference as of the filing date of this application.

Sp Transcription Factors.

In certain aspects the levels of one or more transcription factor belonging to the Sp family of transcription factors can be measured. The Sp family (specificity protein/Krüppel-like factor) is a family of transcription factors that includes the Kruppel-like factors as well as Sp1 (NP_001238754.1 (GI:352962149)), Sp2 (NP_003101.3 (GI:125625357)), Sp3 (NP_001017371.3 (GI:289577125)), Sp4 (NP_003103.2 (GI:67010025)), Sp8 (NP_874359.2 (GI:39812496)), Sp9 (NP_001138722.1 (GI:223646113)), Sp5 (NP_001003845.1 GI:51468067), and Sp7 (NP_001166938.1 (GI: 291045138)). KLF14 (NP_619638.1 (GI:20162554)) is also designated Sp6.

Transcription factor Sp1, also known as Specificity Protein 1, is a human transcription factor involved in gene expression in the early development of an organism. It belongs to the Sp/KLF family of transcription factors. The protein is over 700 amino acids long and contains a zinc finger protein motif, by which it binds directly to DNA and enhances gene transcription. Its zinc fingers are of the Cys2/His2 type. An example of a Sp1 protein is described in GenBank accession NP_001238754.1 (GI:352962149), which is incorporated here by reference as of the filing date of this application.

Transcription factor Sp3 factor belongs to a family of Sp1 related proteins that regulate transcription by binding to consensus GC- and GT-box regulatory elements in target genes. This protein contains a zinc finger DNA-binding domain and several transactivation domains, and has been reported to function as a bifunctional transcription factor that either stimulates or represses the transcription of numerous genes. Transcript variants encoding different isoforms have been described for this gene, and one has been reported to initiate translation from a non-AUG (AUA) start codon. Additional isoforms, resulting from the use of alternate downstream translation initiation sites, have also been noted. An example of a Sp3 protein is described in GenBank accession NP_001017371.3 (GI:289577125), which is incorporated herein by reference as of the filing date of this application. Various isoforms can be readily identified in GenBank.

RON Kinase.

RON is a cell membrane receptor tyrosine kinase, (also known as macrophage-stimulating protein receptor (MST1R)) member of the c-Met family of receptors. RON is a 185-kDa-heterodimeric glycoprotein with disulphide-linked α-chain (35 kDa) and β-chain (150 kDa). It is overexpressed in many cancers, including breast, colon, lung, ovarian, pancreatic and liver cancers (Wagh et al. (2008) *Adv Cancer Res* 100:1-33; Liu et al. (2010) *Carcinogenesis* 31(8): 1456-1464; Thobe et al. (2011) *Oncogene* 30(50): 4990-4998; Gray et al. (2012) *Cancer Letters* 314 (1): 92-101). RON is activated when bound by its ligand, the macrophage-stimulating protein (MSP), also known as hepatocyte growth factor (HGF). Active RON is capable of triggering multiple signaling cascades and its aberrant expression contributes to poor patient survival, and mediates cell cycle progression, angiogenesis and survival of tumor cells. Though RON has been studied in many epithelial tissue-derived tumors, knowledge about its role in prostate cancer is generally lacking. However recent reports show that RON confers enhanced survival in preclinical animal models of prostate cancer. RON's ability to confer enhanced survival could be due to activation of FLIP signaling in prostate tumors. Further since Sp1 can regulate both FLIP and RON, it is possible that RON can be combined with Sp1/Sp3/FLIP signature to predict aggressive prostate cancer and decrease treatment related costs. Interestingly a recent unexpected finding reported translocation of RON to the nucleus without ligand stimulation and homodimerization under conditions of physiological stress. Under these circumstances, RON complexes with EGFR and functions as a transcription factor to regulate gene expression (Liu et al. (2010) *Carcinogenesis* 31(8): 1456-1464). Examples of RON tyrosine kinase include, but are not limited to the protein described in GenBank accession CAA49634.1 (GI: 36110), ACF47618.1 (GI: 194318460), ACF47619.1 (GI: 194318462), ACF47620.1 (GI: 194318464), ACF47621.1 (GI: 194318466), NP_002438.2 (GI: 153946393), and NP_001231866.1 (GI: 349732251), each of which is incorporated herein by references as of the filing date of this application.

RON can be localized at the membrane or in the cytoplasm. However, when examined the expression of RON in the prostate from castrated and sham castrated transgenic adenocarcinoma of the mouse prostate (TRAMP) mice using immunohistochemistry, the inventors discovered RON localization in the nuclear compartment from castrated mice. On the other hand the sham castrated mice exhibited cytoplasmic and membrane localization. Further, colon tumors showed only cytoplasmic staining. In certain aspects, the localization of RON can be used in predicting prostate cancer recurrence, with nuclear localization indicating a greater likelihood of recurrence. RON may form a complex with Sp1/Sp3 or FLIP under certain conditions (castration) and could translocate to the nucleus. In one aspect elevated levels of RON are indicative of an aggressive form of cancer. In other aspects elevated levels of nuclear localized RON is indicative of an aggressive form of cancer.

Gleason Score.

The Gleason Grading system is used to help evaluate the prognosis of men with prostate cancer. A Gleason score is given to prostate cancer based upon its microscopic appearance. Cancers with a higher Gleason score are more aggressive and have a worse prognosis. Typically a urologist or radiologist will remove a cylindrical sample (biopsy) of prostate tissue through the rectum, using hollow needles, and prepare microscope slides. The pathologist assigns a first grade to the most common tumor pattern (the first grade or primary grade represents the majority of tumor (has to be greater than 50% of the total pattern seen)), and a second grade (the second grade relates to the minority of the tumor (has to be less than 50%, but at least 5%, of the pattern of the total cancer observed)) to the next most common tumor pattern. The two grades are added together to get a Gleason Score. For example, if the most common tumor pattern was grade 3, and the next most common tumor pattern was grade 4, the Gleason Score would be 3+4=7. The Gleason Grade ranges from 1 to 5, with 5 having the worst prognosis. The Gleason Score ranges from 2 to 10, with 10 having the worst prognosis. For Gleason Score 7, a Gleason 4+3 is a more aggressive cancer than a Gleason 3+4.

Gleason patterns are associated with the following features: (a) Pattern 1—The cancerous prostate closely resembles normal prostate tissue. The glands are small, well-formed, and closely packed. (b) Pattern 2—The tissue still has well-formed glands, but they are larger and have more tissue between them. (c) Pattern 3—The tissue still has recognizable glands, but the cells are darker. At high magnification, some of these cells have left the glands and are beginning to invade the surrounding tissue. (d) Pattern 4—The tissue has few recognizable glands. Many cells are invading the surrounding tissue. (e) Pattern 5—The tissue does not have recognizable glands. There are often just sheets of cells throughout the surrounding tissue.

II. METHODS OF DETECTION

In certain aspects, the biomarkers of this invention can be measured or detected by immunoassay, which includes immune reagent capture followed by further analysis, e.g., mass spectrometry. Immunoassays use biospecific capture reagents or binding agents, such as antibodies, to capture biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized or recombinantly produced for use in generating antibodies.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains, Fab, Fab' F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins.

In certain aspects, immunoassays are contemplated, for example, sandwich immunoassays including ELISA or fluorescence-based immunoassays, as well as other enzyme immunoassays. In a SELDI-based immunoassay, a biospecific capture reagent for the biomarker is attached to the surface of a mass spectrometry (MS) probe, such as a pre-activated ProteinChip array. The biomarker is then specifically captured on the biochip through this reagent, and the captured biomarker is detected by mass spectrometry.

A. Immunohistochemistry ("IHC")

In particular embodiments of the invention, the expression of FLIP, transcription factor Sp1, and/or transcription factor Sp3 proteins in a sample is examined using immunohistochemistry protocols. Immunohistochemical staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods.

For sample preparation, a tissue or cell sample from a mammal (typically a human patient) may be used. Examples of samples include, but are not limited to, cancer cells such as colon, breast, prostate, ovary, lung, stomach, pancreas, lymphoma, and leukemia cancer cells. The sample can be obtained by a variety of procedures known in the art including, but not limited to surgical excision, aspiration, or biopsy. The tissue may be fresh or frozen. In one embodiment, the sample is fixed and embedded in paraffin or the like.

The tissue sample may be fixed (i.e. preserved) by conventional methodology (See e.g., "Manual of Histological Staining Method of the Armed Forces Institute of Pathology," 3rd edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's, or paraformaldehyde may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by one of several standard methods. Examples of slide adhesives include, but are not limited to silane, gelatin, poly-L-lysine, and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

Optionally, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen (e.g., FLIP, transcription factor Sp1, and/or transcription factor Sp3 proteins) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting or exposure to radiographic film.

(b) Colloidal gold particles.

(c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in Current Protocols in Immunology, supra, for example. Fluorescence can be detected using a fluorimeter or photographic film.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody.

The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during, or following IHC may be desired, For example, epitope retrieval methods, such as heating the tissue sample in citrate buffer may be carried out (see, e.g., Leong et al. (1996) *Appl. Immunohistochem.* 4 (3):201).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody that binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope, and staining intensity criteria, routinely used in the art, may be employed.

Any suitable means of measuring expression levels of RNA products can be used in accordance with the methods described herein. For example, the methods may utilize a variety of polynucleotides that specifically hybridize to one or more FLIP, transcription factor Sp1, or transcription factor Sp3 RNA products including, for example, oligonucleotides, cDNA, DNA, RNA, PCR products, synthetic DNA, synthetic RNA, or other combinations of naturally occurring of modified nucleotides which specifically hybridize to one or more of the RNA products. Such polynucleotides may be used in combination with the methods to measure RNA expression described further herein including, for example, array hybridization, RT-PCR, nuclease protection and northern blots.

In certain embodiments, array hybridization may be used to evaluate levels of FLIP, transcription factor Sp1, transcription factor Sp3 or RON RNA expression. Array hybridization utilizes nucleic acid members stably associated with a support that can hybridize with FLIP, transcription factor Sp1, transcription factor Sp3, or RON RNA expression products. The length of a nucleic acid member attached to the array can range from 8 to 1000 nucleotides in length and are chosen so as to be specific for the FLIP, transcription factor Sp1, transcription factor Sp3, or RON RNA products. The nucleic acid members may be RNA or DNA, single or double stranded, and/or may be oligonucleotides or PCR fragments amplified from cDNA. Preferably oligonucleotides are approximately 10-100, 10-50, 20-50, or 20-30 nucleotides in length. Portions of the expressed regions of FLIP, transcription factor Sp1, transcription factor Sp3, or RON can be utilized as probes on the array. More particularly oligonucleotides complementary to FLIP, transcription factor Sp1, transcription factor Sp3, or RON genes and or cDNAs derived from the FLIP, transcription factor Sp1, transcription factor Sp3, or RON genes are useful. For oligonucleotide-based arrays, the selection of oligonucleotides corresponding to the gene of interest are useful as probes, which is well understood in the art. More particularly it is important to choose regions that will permit hybridization to the target nucleic acids. Factors such as the Tm of the oligonucleotide, the percent GC content, the degree of secondary structure and the length of nucleic acid are important factors. See for example U.S. Pat. No. 6,551, 784.

Arrays may be constructed, custom ordered, or purchased from a commercial vendor. Various methods for constructing arrays are well known in the art. For example, methods and techniques applicable to oligonucleotide synthesis on a solid support, e.g., in an array format have been described, for example, in WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752 and Zhou et al., Nucleic Acids Res. 32: 5409-5417 (2004).

In some embodiments, target nucleic acids from a test sample are amplified and the levels quantitated. Amplification of target nucleic acids can be performed by any means known in the art. In some cases, target nucleic acids are amplified by polymerase chain reaction (PCR). Examples of PCR techniques that can be used include, but are not limited to, quantitative PCR, quantitative fluorescent PCR (QF-PCR), multiplex fluorescent PCR (MF-PCR), real time PCR(RT-PCR), an single cell PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242, 794; 5,494,810; 4,988,617; and 6,582,938.

III. METHODS OF TREATMENT

Based on the determination using the target proteins described herein a physician or other medical profession can treat the cancer with an appropriate therapy. Such therapies include:

A. Surgery

Surgery is the removal of the tumor and surrounding tissue during an operation. It is used to try to cure cancer before it has spread outside the prostate. The type of surgery depends on the stage of the disease, the man's general health, and other factors. Surgical options include:

Radical Prostatectomy.

A radical prostatectomy is the surgical removal of the whole prostate and seminal vesicles. Nerve-sparing surgery, when possible, increases the chance that a man can maintain his sexual function after surgery by avoiding surgical damage to the nerves that allow erections and orgasm to occur.

Laparoscopic Prostatectomy.

This type of surgery can be much less invasive than an open radical prostatectomy and may shorten recovery time. A camera and instruments are inserted through small, keyhole incisions in the patient's abdomen. The surgeon then directs the instruments to remove the prostate gland and surrounding tissue.

Transurethral Resection of the Prostate (TURP).

TURP is most often used to relieve symptoms of a urinary blockage, not to cure cancer. In this procedure, with the patient under a full anesthetic, a surgeon inserts a cystoscope (a narrow tube with a cutting device) into the urethra and into the prostate to remove prostate tissue. This is rarely used to treat prostate cancer.

Cryosurgery.

Cryosurgery (also called cryotherapy or cryoablation) is the freezing of cancer cells with a metal probe inserted through a small incision in the area between the rectum and the scrotum. Cryosurgery may be useful for early-stage cancer and for men who cannot have a radical prostatectomy.

B. Radiation Therapy

Radiation therapy is the use of high-energy radiation to kill cancer cells. The most common type of radiation treatment is called external-beam radiation therapy, which is radiation given from a machine outside the body. When radiation treatment is given using implants, it is called internal radiation therapy or brachytherapy. A radiation therapy regimen (schedule) usually consists of a specific number of treatments given over a set period of time.

External-Beam Radiation Therapy.

External-beam radiation therapy focuses a beam of radiation on the area with the cancer. Some cancer centers use conformal radiation therapy (CRT), in which computers help precisely map the location and shape of the cancer. CRT reduces radiation damage to healthy tissues and organs around the tumor by directing the radiation therapy beam from different directions to focus the dose on the tumor. External-beam radiation therapy is usually given with a high-energy x-ray beam. It can also be given with proton therapy (also called proton beam therapy), which uses protons rather than x-rays. At high energy, protons can destroy cancer cells.

Intensity-Modulated Radiation Therapy (IMRT).

IMRT is a type of three-dimensional (3-D) CRT. CRT uses CT scans to form a 3-D picture of the prostate before treatment. With IMRT, high doses of radiation can be directed at the prostate without increasing the risk of damaging nearby organs.

Brachytherapy.

Brachytherapy is the insertion of radioactive sources directly into the prostate. These sources (called seeds) give off radiation just around the area in which they are inserted and may be used for hours (high-dose rate) or for weeks (low-dose rate). Low-dose rate seeds are left in the prostate permanently, even after all the radioactive material has been used up.

C. Hormone Therapy

Because prostate cancer growth is driven by the male hormones (androgens), lowering levels of these hormones can help slow the growth of the cancer. Hormone treatment is also called androgen ablation or androgen-deprivation therapy. The most common androgen is testosterone. Testosterone levels in the body can be lowered either surgically, with surgical castration (removal of the testicles), with drugs that turn off the function of the testicles, or with drugs that block androgen action. Hormone therapy is used to treat prostate cancer in different situations, including cancers that have come back after surgery and radiation therapy, or if it has spread throughout the body at any time.

Recent research has shown that hormone therapy can help lengthen lives when used with radiation therapy for a prostate cancer that is more likely to recur. For some men, hormone therapy will be used first to shrink a tumor before radiation therapy or surgery. In some men with prostate cancer that has spread locally, called locally advanced or high-risk prostate cancer, hormone therapy is given before, during, and after radiation therapy. Hormone therapy should also be considered for men who have prostate cancer that has spread to the lymph nodes (found after radical prostatectomy) as adjuvant therapy (treatment that is given after the first treatment). It may also be given to men with intermediate-risk or high-risk cancer. Hormone therapies include:

Bilateral Orchiectomy.

Bilateral orchiectomy is the surgical removal of both testicles.

LHRH Agonists.

LHRH stands for luteinizing hormone-releasing hormone. LHRH agonists are drugs that reduce the body's production of testosterone by interfering with hormonal control mechanisms within the brain, which control the functioning of the testicles.

LHRH Antagonist.

This type of drug, also called a gonadotropin-releasing hormone (GnRH) antagonist, stops the testicles from producing testosterone by inhibiting LHRH. The FDA has approved one drug, degarelix (Firmagon), given by injection, to treat advanced prostate cancer.

Anti-Androgens.

While LHRH agonists lower testosterone levels in the blood, anti-androgens block testosterone from binding to androgen receptors in the cancer.

Combined Androgen Blockade.

LHRH agonists can be used in combination with peripheral-blocking drugs, such as anti-androgens, to more completely block male hormones.

CYP-17 Inhibitors.

CYP-17 inhibitors are a type of hormone therapy that prevents androgen from being made by the body. Abiraterone (Zytiga) is a CYP-17 inhibitor that has been approved by the FDA as a treatment for castration-resistant prostate cancer that has spread when chemotherapy with docetaxel (Docefrez, Taxotere) has not worked.

D. Recurrent Prostate Cancer

A remission is when cancer cannot be detected in the body and there are no symptoms. This may also be called "no evidence of disease" or NED. Treatments that help prevent a recurrence include androgen deprivation therapy and radiation therapy. If a cancer returns after being treated, it is called recurrent cancer. It may come back in the same place (called a local recurrence), nearby (regional recurrence), or in another place (distant recurrence). Also, as described herein, an increasing PSA level may be a sign of prostate cancer recurrence even if no tumor can be found.

The choice of treatment plan is based on the cancer's stage and may include the therapies described above (such as surgery, radiation therapy, and hormone therapy) but may be used in a different combination or given at a different pace.

E. Metastatic (Advanced) Prostate Cancer

If the cancer has spread to another location in the body, it is a metastatic cancer. The standard treatment for metastatic prostate cancer is hormone therapy. Generally, prostate cancer will develop the ability to grow without using male sex hormones. This is a castration-resistant prostate cancer. Recommend treatment plans for recurrent cancer include vaccine therapy with sipuleucel-T (Provenge), chemotherapy with docetaxel, or clinical trials.

Vaccine Therapy.

Sipuleucel-T (Provenge) is a form of immunotherapy (also called biologic therapy) that is designed to boost the body's natural defenses to fight the cancer. It uses materials made either by the body or in a laboratory to bolster, target, or restore immune system function.

Chemotherapy.

Chemotherapy is the use of drugs to kill cancer cells, usually by stopping the cancer cells' ability to grow and divide. Systemic chemotherapy is delivered through the bloodstream to reach cancer cells throughout the body. A chemotherapy regimen (schedule) usually consists of a specific number of cycles given over a set period of time. A patient may receive one drug at a time or combinations of different drugs at the same time.

Chemotherapy for prostate cancer is given intravenously (injected into a vein), and it may help patients with advanced or hormone-refractory prostate cancer. There are several standard drugs used for prostate cancer. The first drug used is often docetaxel given with a steroid called prednisone (multiple brand names). This combination has been shown to help men with advanced prostate cancer live longer than another chemotherapy, mitoxantrone (Novantrone), which is most useful for controlling pain from the cancer.

Chemotherapies include, but are not limited to mitoxantrone, docetaxel, and cabazitaxel (Jevtana) for use in men with prostate cancer in specific situations, such as prostate cancer that is resistant to hormone therapy. Cabazitaxel is similar to docetaxel, but research studies have shown that it can be effective for prostate cancer that is resistant to docetaxel. The side effects are similar to docetaxel and include low white blood cell counts, increased risk of infections, allergic reactions, nausea, vomiting, diarrhea, and kidney and liver problems.

IV. KITS

In another aspect, the present invention provides kits for diagnosis or prognosis of cancer, which kits are used to detect biomarkers described herein. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

V. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figures 2A, 2B:
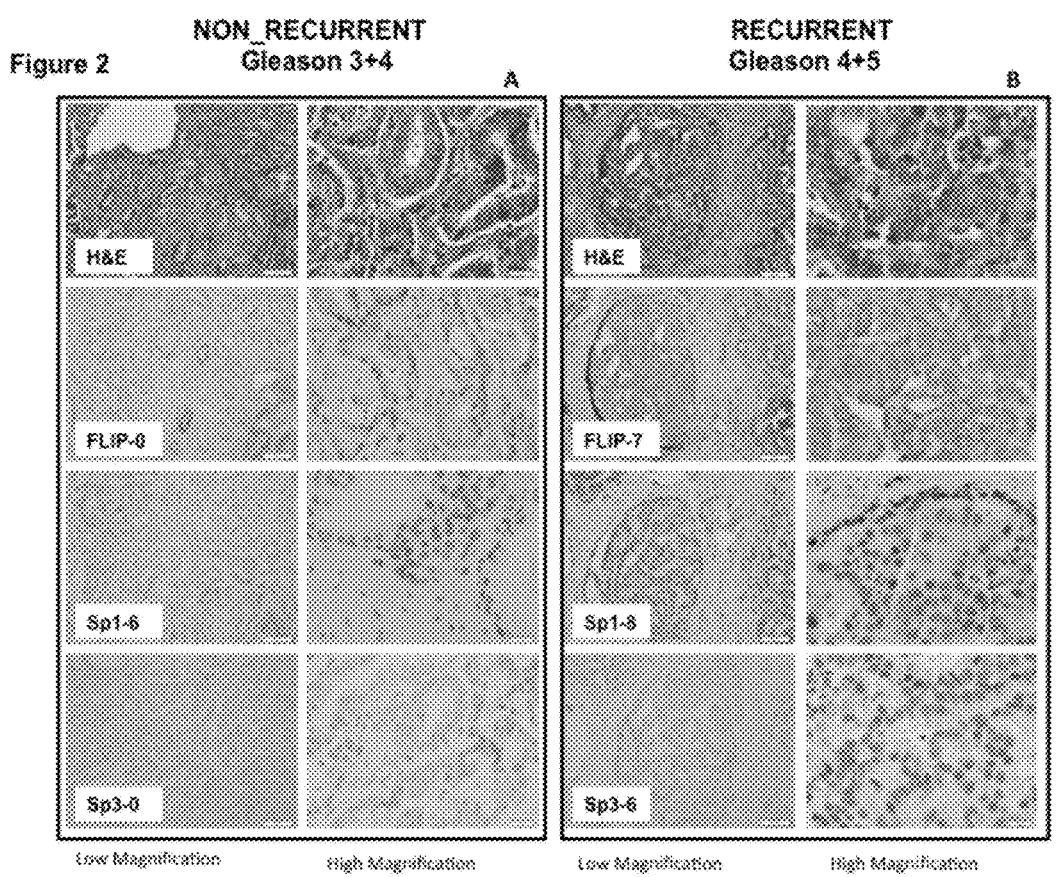
FIG. 2. (A). H&E staining and IHC analysis of expression of FLIP, Sp1, and Sp3 in a representative sample of non-recurrent PCA [Gleason 7 (3+4)] under low magnification (left) and high magnification (right). The total score for this sample was 0, 6, and 0 for FLIP, Sp1, and Sp3 respectively. (B). H&E and IHC staining of FLIP, Sp1 and Sp3 in a representative sample from a patient with recurrent PCA [(Gleason 9 (4+5)] under low magnification (left) and high magnification (right). The total score for this sample was 7, 8, and 6 for FLIP, Sp1, and Sp3, respectively.
Figure 3A:
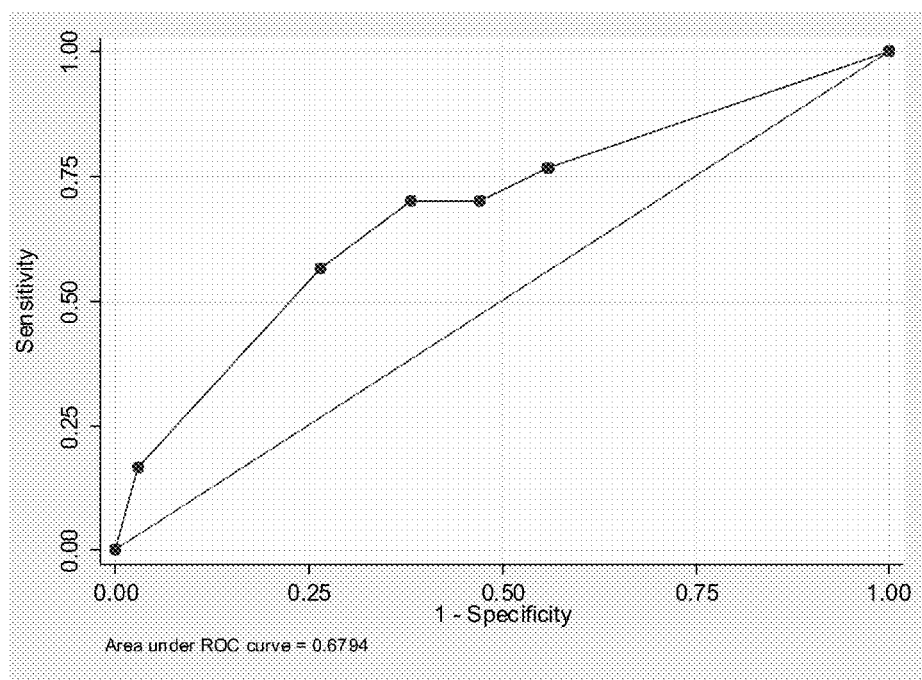
FIGS. 3A-3D. Plot of sensitivity versus specificity. Area under the ROC curves calculated for (A) FLIP (0.71), (B) Sp1 (0.66), (C) Sp3 (0.68), and (D) Gleason (0.76) show various degrees of discrimination as predictors of recurrence. An area under the ROC curve of 0.8 to 1.0 is considered to be very good to excellent discrimination, whereas 0.5 indicates no discrimination.
Figure 3B:
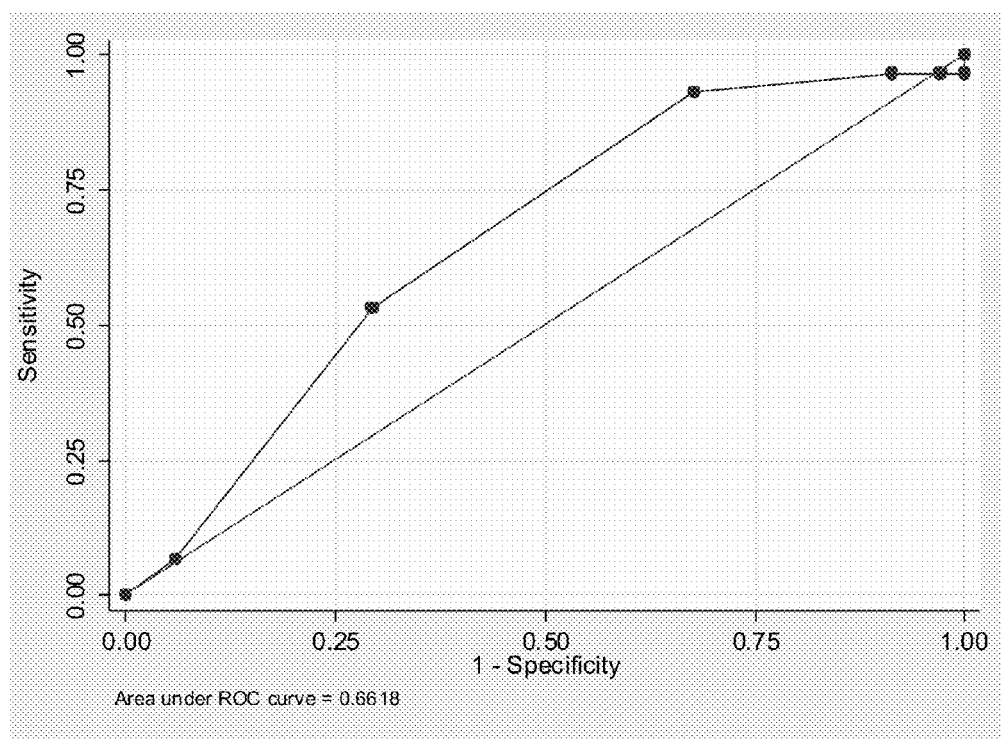
Figure 3C:
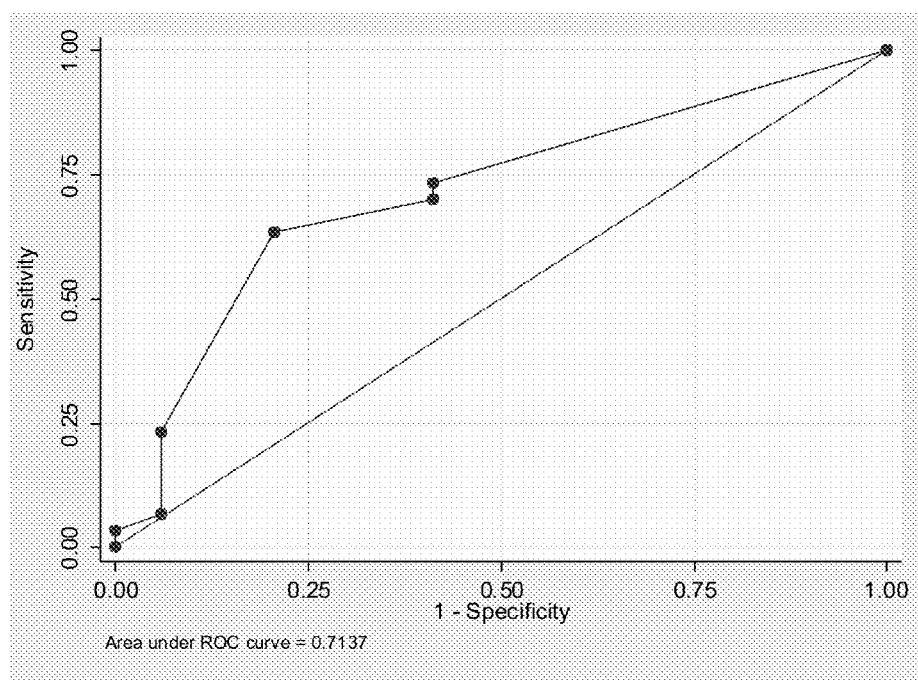
Figure 3D:
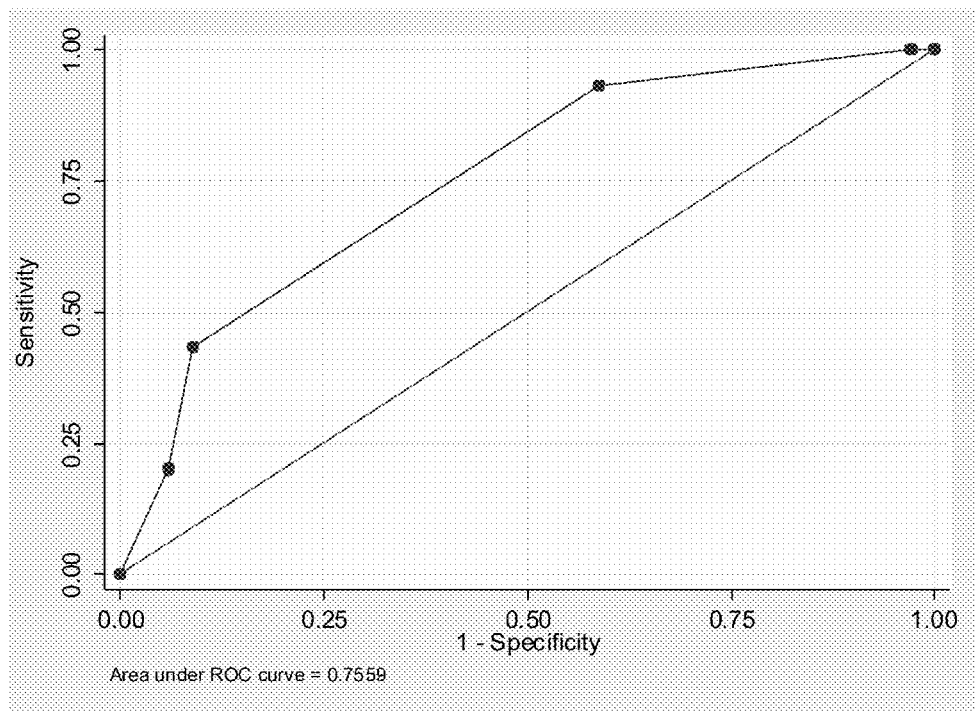

The inventors assessed the expression of the anti-apoptotic protein FLIP and its transcription regulators Sp1 and Sp3 by immunohistochemical evaluation of tissue samples obtained from 64 patients who underwent radical prostatectomy as primary treatment for prostate cancer. Patients had at least 60 months follow-up with PSA measurements and only those with an undetectable PSA at 60 months were considered to have non-recurrent disease. Increasing levels of PSA after prostatectomy were used as a surrogate endpoint for poor outcome. PSA non-failure was defined as PSA levels undetectable or <0.2 ng/mL for at least 5 years after prostatectomy and no other signs of recurrence such as metastasis. PSA failure was defined as a PSA level >0.2 ng/mL that increased during the 5 years after prostatectomy (Hosmer and Lemeshow (2000) Applied Logistic Regression. 2nd ed. New York, N.Y.: John Wiley & Sons, Inc.). Due to limited sample size only two-way interactions were considered and PSA was not added to the Gleason score. First, the expression of FLIP, Sp1, and Sp3 was compared between the two groups using immunohistochemistry and significant differences were found between PSA failure and non-failure groups in the expression of FLIP, Sp3, and Sp1 (Wilcoxon rank-sum; FIG. 1 and FIG. 2). As shown in the box plots in FIG. 1, significant differences were found in the mean total IHC score between the non-recurrent and recurrent cases for Sp1 (p=0.019), Sp3 (p=0.011), and FLIP (p=0.0019). Gleason score was included in the analysis because this will have an influence on the outcome. Gleason scores for our 64-patient cohort were significantly different in the recurrent and non-recurrent groups (p=0.0001; data not shown). It should be mentioned that this is not necessarily the case as studies have shown that Gleason grade 7 by itself may not be significant (Herman et al. (2001) *Am J Surg Pathol* 25: 657-660). In our cohort, 50% of prostatectomy cases were Gleason 7: (29.69% were 3+4 and 20.3% were 4+3). Of the 29.69% that were 3+4, 41.2% were non-recurrent and 16.67% were recurrent cases. On the other hand, of the 20.3% with the more aggressive 4+3 grading, 8.8% were non-recurrent and 33.33% were recurrent. These data suggest that the differences in FLIP, Sp1, and Sp3 between the recurrent and non-recurrent groups are significant.

Based on the significant differences observed between recurrent and non-recurrent groups, the inventors next calculated the sensitivity and specificity of the generated data (Herman et al. (2001) *Am J Surg Pathol* 25: 657-660;

Kreisberg et al. (2004) *Cancer Res* 64: 5232-5236). Univariate logistic regression of FLIP, Sp1, Sp3, and Gleason grade resulted in AUCs for ROC curves of 0.71, 0.66, 0.68, and 0.76, respectively (FIG. 3).

Figure 4:
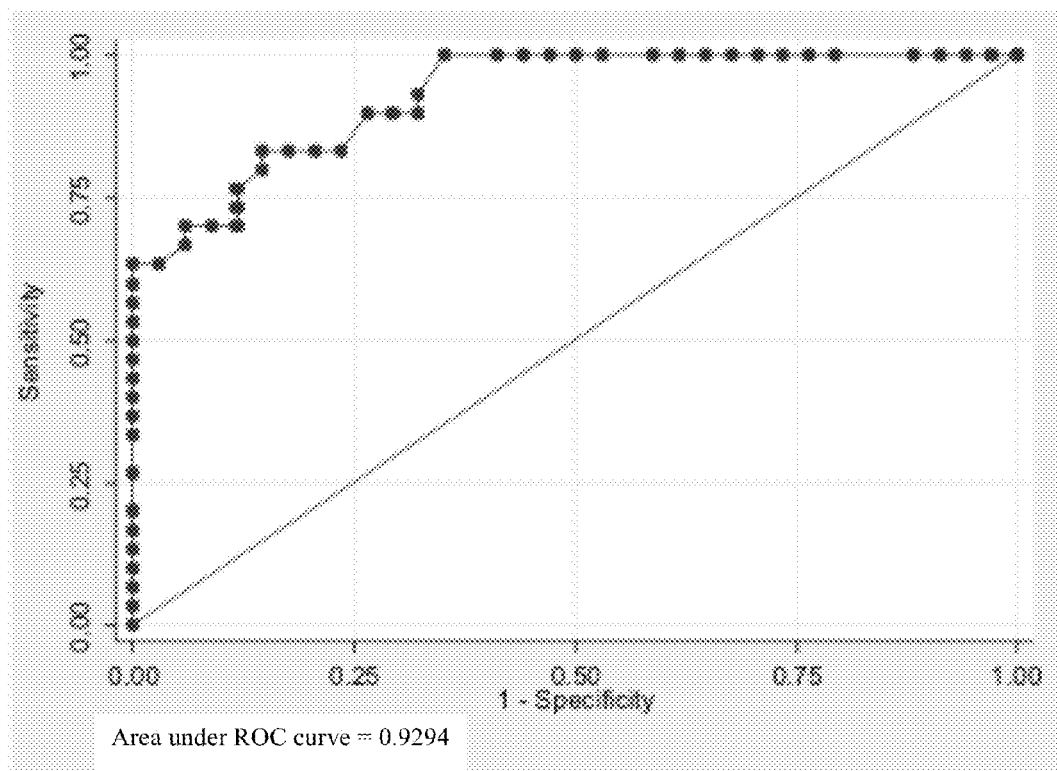
FIG. 4. Plot of sensitivity versus specificity. Area under the ROC curves calculated for combination of FLIP, Sp1, Sp3, Gleason score, and their interactions gives a value of 0.93 indicating excellent discrimination between non-recurrent and recurrent cases.
Figure 5:
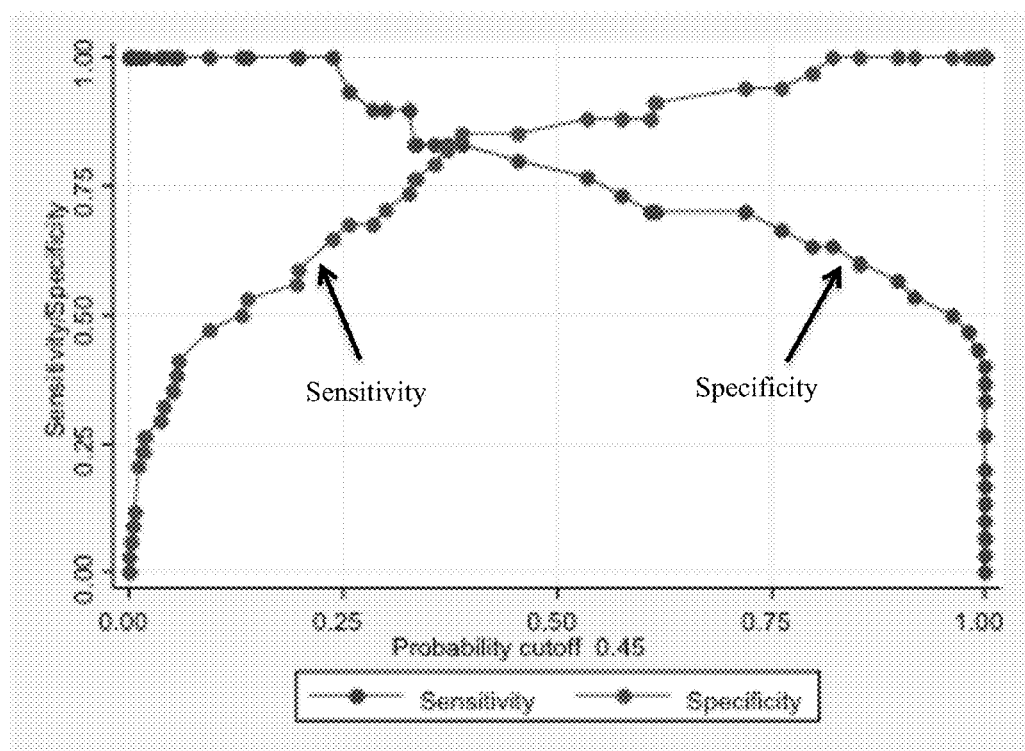
FIG. 5. At a probability cut-off point of 0.45 both the sensitivity (80%) and specificity (85.3%) for this combination of markers is high, indicating excellent discrimination power of the combination.
Figure 6A:
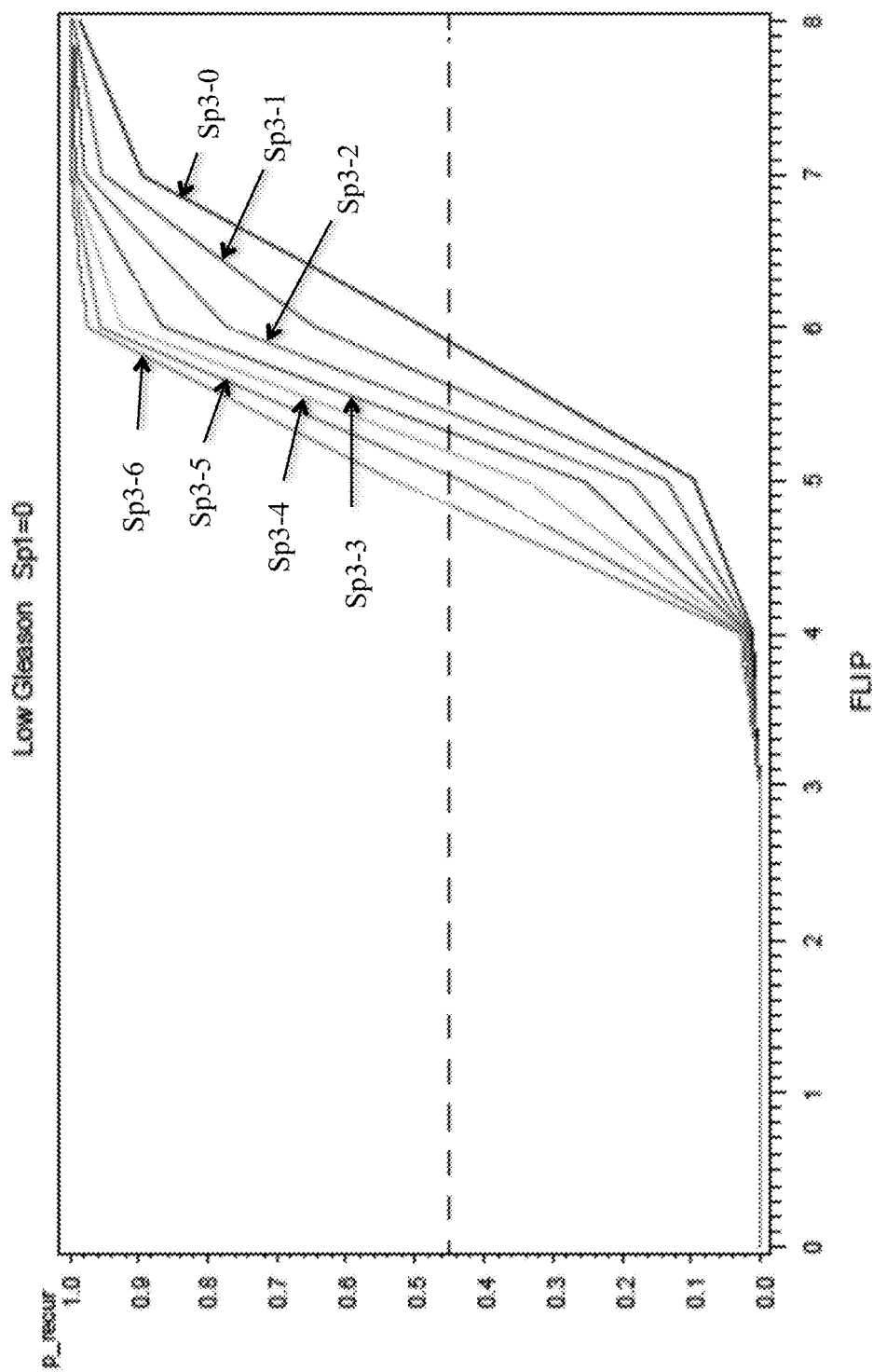
FIGS. 6A-6F. Predicted probability of recurrence when Gleason is low grade 5-7(3+4) for different levels of Sp1 (0 (A), 3 (B), and 6 (C)) and Sp3 (0 (D), 3 (E), and 6 (F)) as a function of FLIP (0-8) interaction. Cases above the cut-off point of 0.45 (dashed line) are predicted to recur. The interaction of FLIP and Sp3 is shown as solid lines on the X-axis. Predicted probability of recurrence when Gleason is high grade 7 (4+3) for different levels of Sp1 (0, 3, and 6) and Sp3 (0, 3, and 6) as a function of FLIP (0-8) interaction. Cases above the cut-off point of 0.45 (dashed line) are predicted to recur. The interaction of FLIP and Sp3 is shown as solid lines on the X-axis.
Figure 6B:
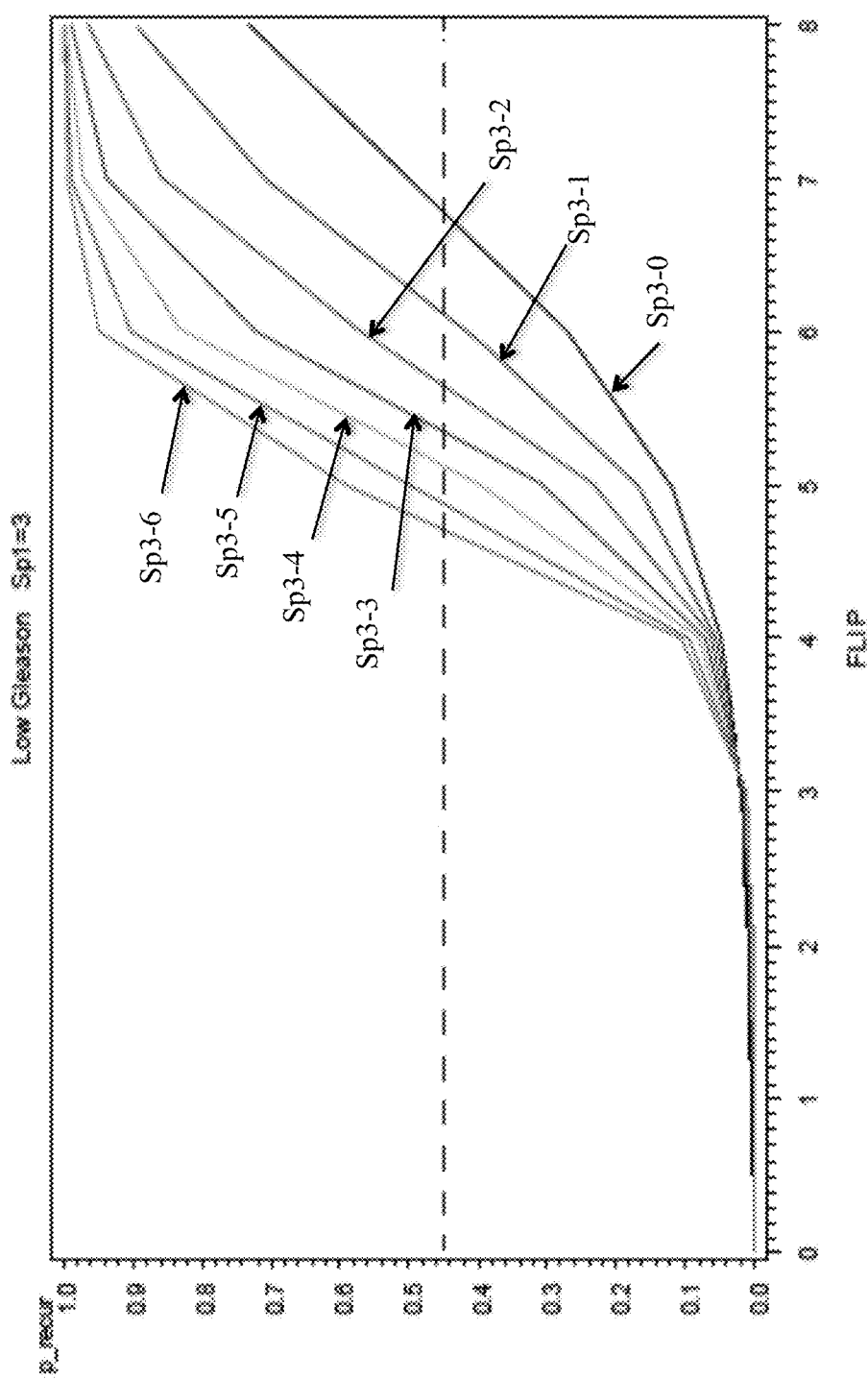
Figure 6C:
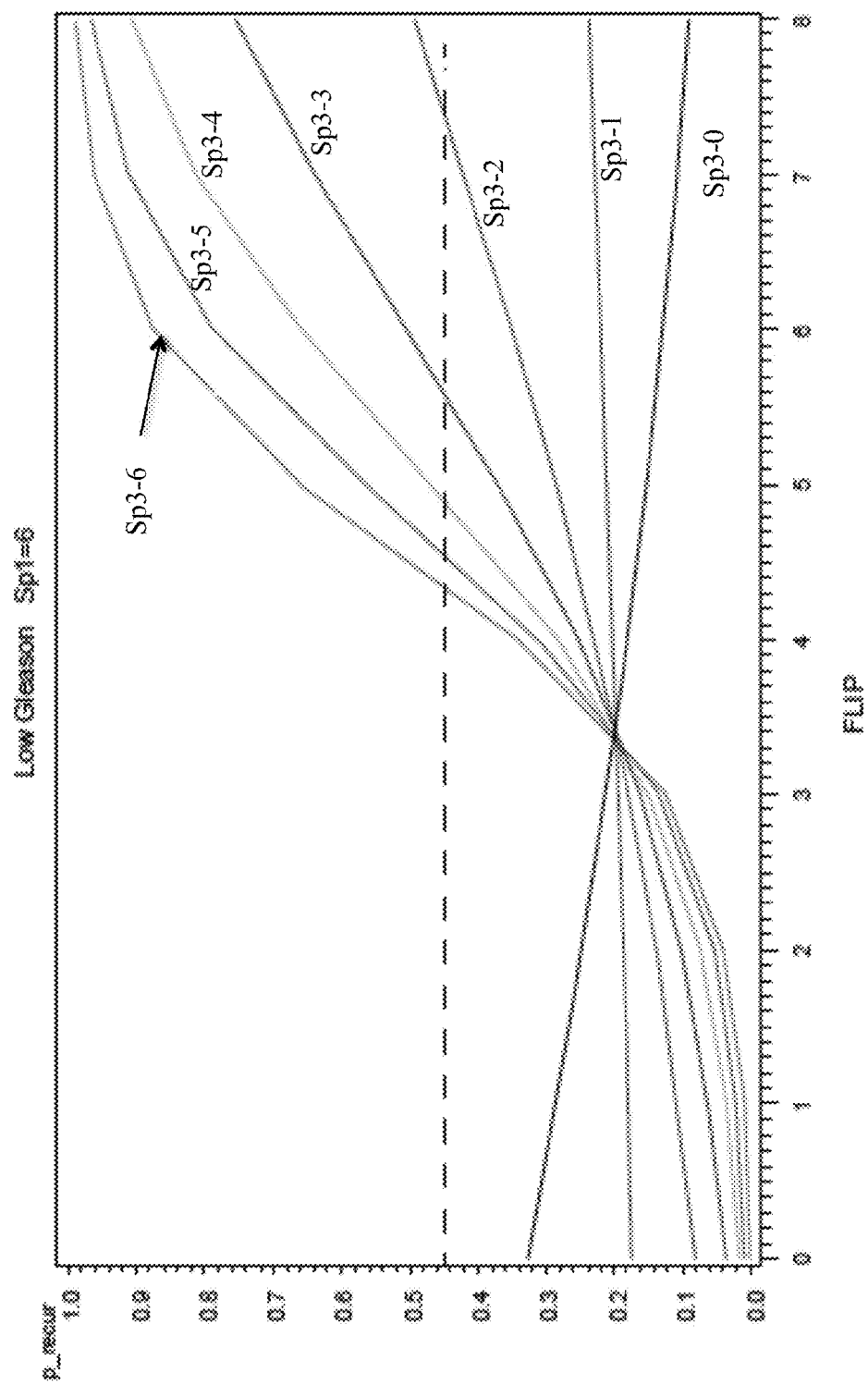
Figure 6D:
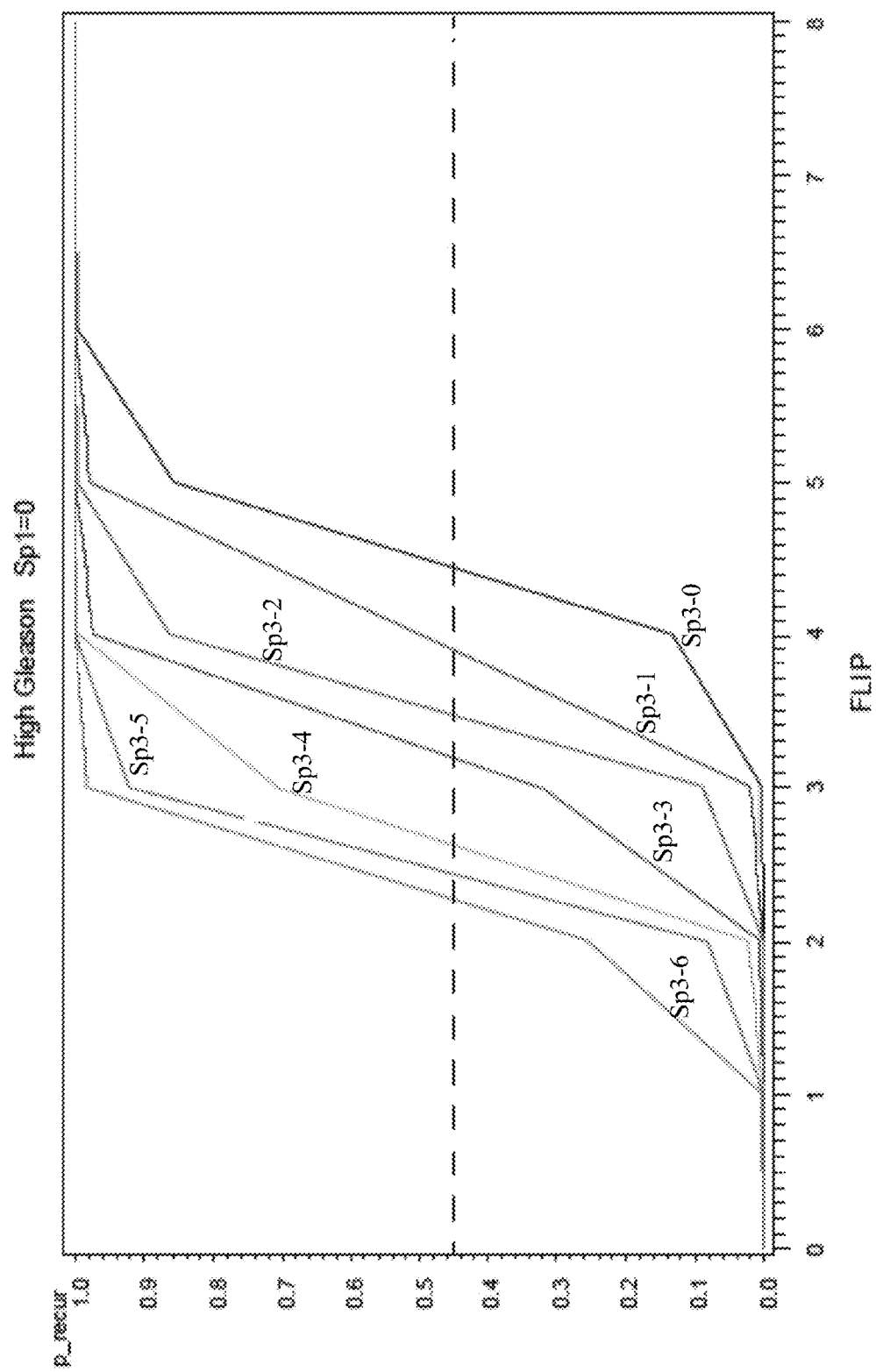
Figure 6E:
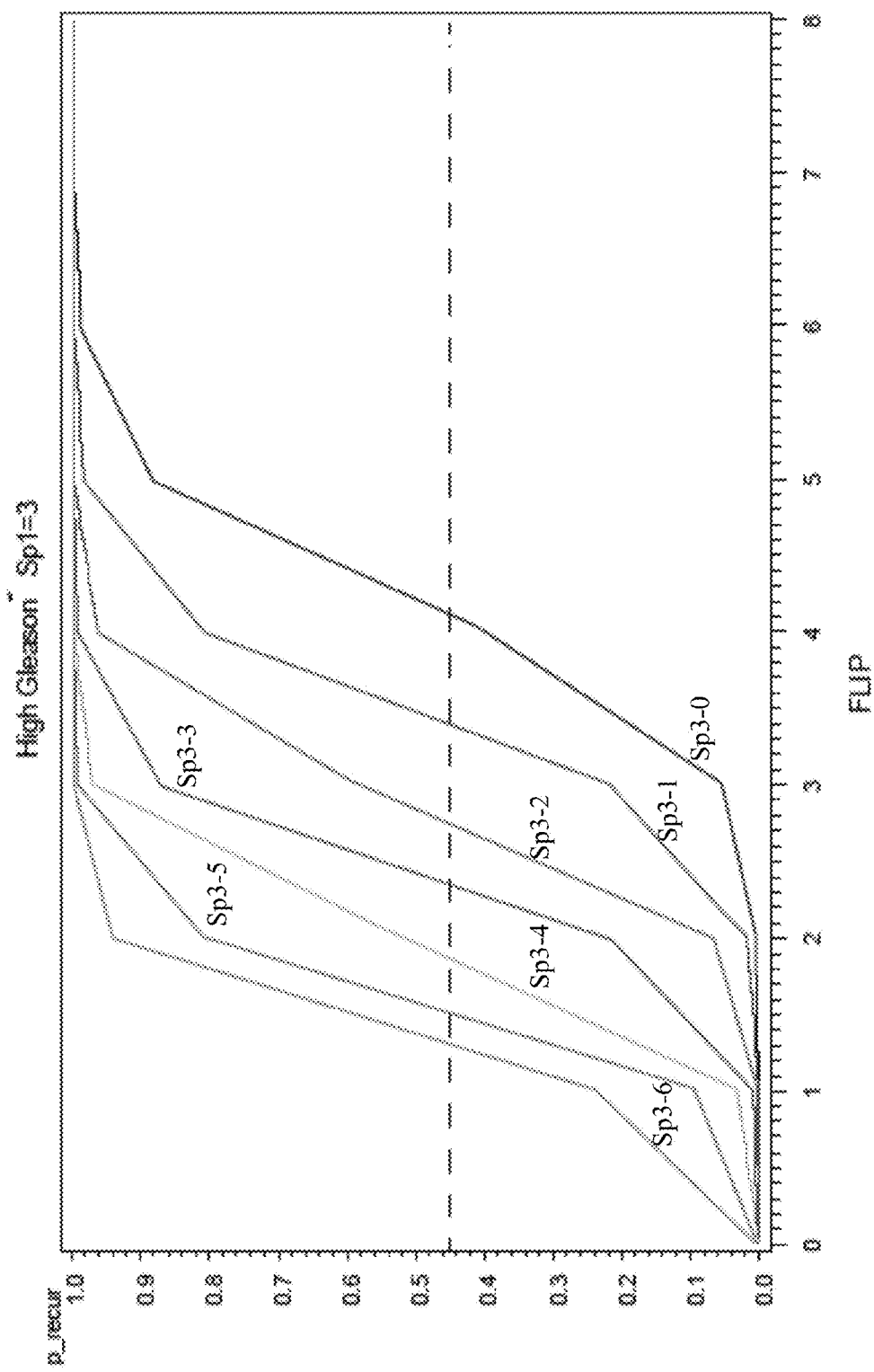
Figure 6F:
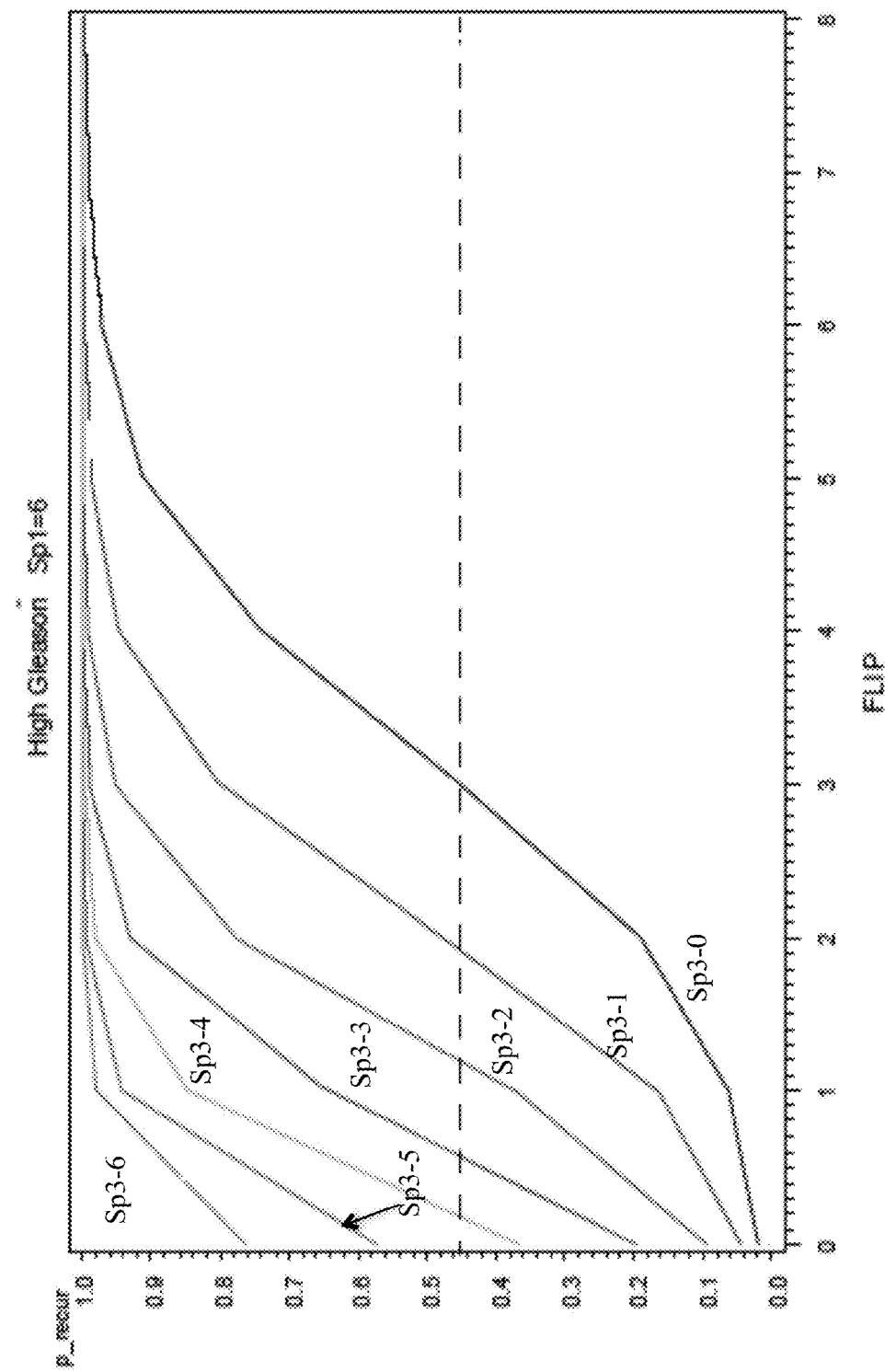
Figures 7A, 7B, 7C:
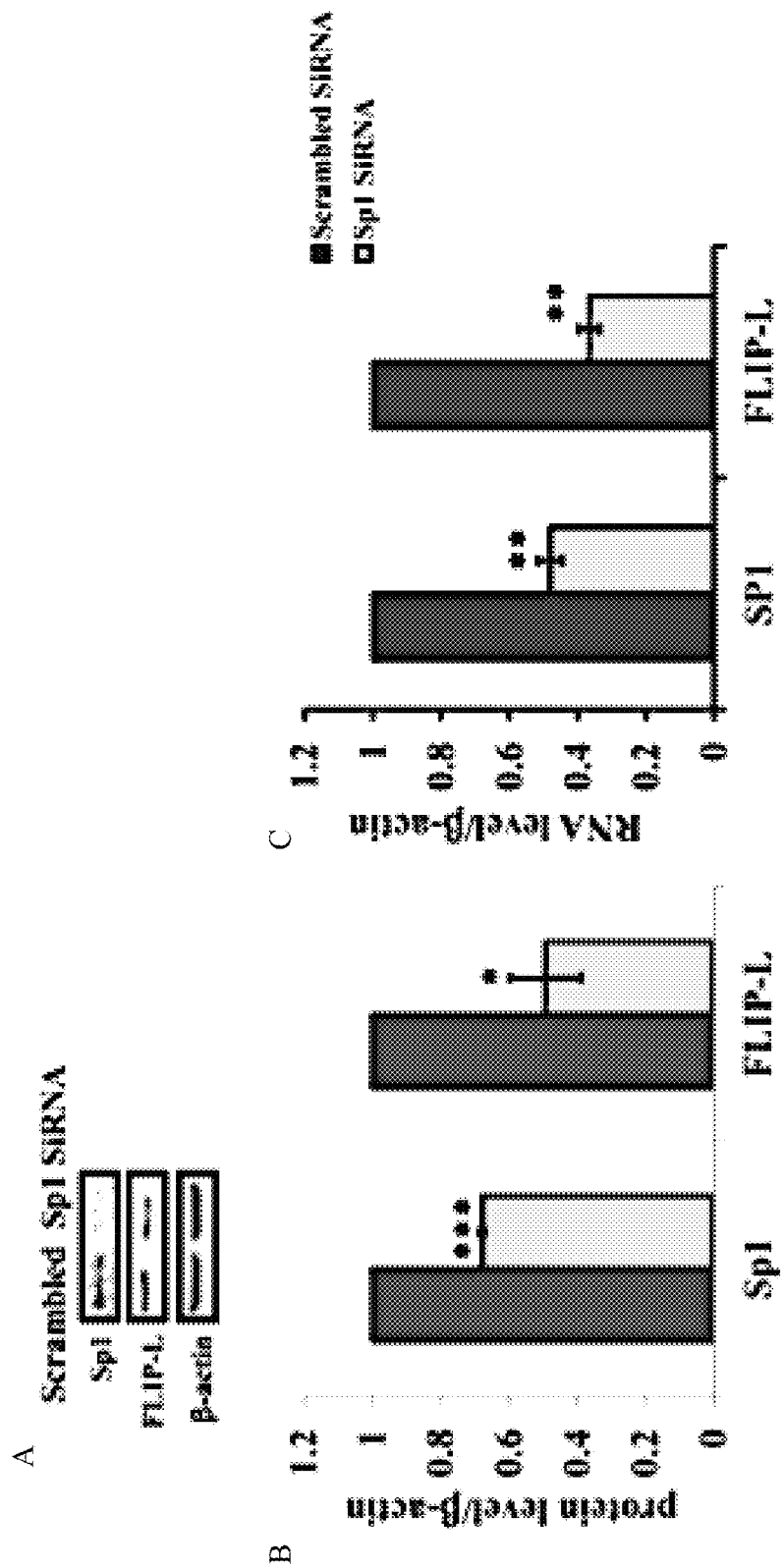
FIGS. 7A-7C. Sp1 regulates FLIP expression in androgen-independent PC-3 cells. (A) Sp1 siRNA was used to knock down Sp1 expression is PC3 cells. Following 48 h transfection, RNA and protein were extracted and subjected to (B) real-time PCR and (C) western blotting, respectively. The data presented are an average of three independent experiments conducted in duplicate.

Given the above results the inventors explored the prognostic value of the markers using a multivariable logistic model with a backward selection that included Gleason score (high vs. low) (p=0.14), FLIP (p=0.07), and Sp1 (p=0.08) as main effects and the interactions of FLIP with Sp3 (p=0.02), Sp1 (0.11), and Gleason (p=0.03), as well as the interaction of Sp3 and Gleason (p=0.014), as second-term effects. These interactions were significantly different between non-recurrent and recurrent groups. Variables with p<0.15 were retained for the Hosmer-Lemeshow Goodness of Fit model, using PSA failure vs. non-failure as the dependent variable. The model showed a good fit, with chi-square value of 8.8 and p=0.4, with an AUC for the ROC curve of 0.93 (FIG. 4). At the optimum cut-off point of 0.45, the sensitivity was 80% and specificity was 85.29%, resulting in correct classification in 83% of the cases (FIG. 5).

FIG. 6 shows patients that are predicted to recur based on these biomarkers. Both Gleason and PSA alone have sensitivities below 80% therefore this model is an improvement on the markers currently in use. The logistic regression prediction plot shows that a combination of FLIP, Sp1, and Sp3 in addition to Gleason is prognostic of PSA failure and non-failure. When the model results are plotted with the predicted probability of recurrence on the Y-axis and the interaction of FLIP-Sp3 by Gleason grade (low or high) on the X-axis, the impact of interaction between the two markers and the influence of the Gleason grade can be seen, and also the influence of Sp1 at three levels (total score of 0, 3, and 6). In FIGS. 6A and 6B, all cases above the cut-off point of 0.45 (dashed line) are predicted to be recurrent. With each increase in the staining score of Sp3, together with an increase in FLIP, the risk of recurrence goes up even with a low Gleason grade of 5-7 (3+4). However, when Gleason grade is high 7 (4+3)-9 and Sp1 is high (6), the risk increases dramatically. When FLIP is 4 (range 0-8) and Gleason grade is high, both Sp3 and Sp1 need to be near 0 for a case to be non-recurrent, but when the Sp1 score is 3, cases with a FLIP score of 4 are recurrent when Sp3 is ≥1 (FIGS. 6A and 6B). This model shows that FLIP, Sp1, and Sp3 levels in conjunction with Gleason grade is a good predictor of the risk of recurrence after radical prostatectomy. FIG. 6 indicates that for a given value of Sp3 score (independent of Sp1 score), the predicted probability of recurrence increases with increasing FLIP staining when the Gleason score was low, suggesting potential interaction. On the other hand, when the Gleason score was high, although the predicted probability of recurrence increased with FLIP staining when the Sp1 score was 0 or 3, when the Sp1 score was 6, the inventors did not see this interaction, suggesting that Gleason and Sp3 are sufficient for predicting recurrence (Table 2).

TABLE 2

| | A-Univariate | | | B-Multivariate | | |
|---|---|---|---|---|---|---|
| Marker | Odds Ratio | P > \|z\| | 95% Conf. Interval | Markers | Odds Ratio | P > \|z\| | 95% Conf. Interval |
| Sp1 | 1.4 | 0.162 | 0.87-2.25 | Sp1 | 8.08 | 0.08 | 0.80-81.4 |
| FLIP | 1.43 | 0.005 | 1.1-1.84 | FLIP | 18.7 | 0.07 | 0.79-443.9 |
| Sp3 | 1.3 | 0.018 | 1.05-1.65 | Gleason | 0.04 | 0.14 | 0.006-2.85 |
| Gleason | 3.3 | 0.001 | 1.6-6.7 | Gleason* FLIP | 4.3 | 0.03* | 1.15-16.04 |
| Gleason gps | 2.2 | 0.0001 | 1.47-3.29 | Gleason* Sp3 | 5.55 | 0.01* | 1.41-21.82 |
| | | | | Sp1* FLIP | 0.67 | 0.11 | 0.41-1.1 |
| | | | | Sp3* FLIP | 1.28 | 0.02* | 1.04-1.58 |

Figures 8A, 8B, 8C, 8D:
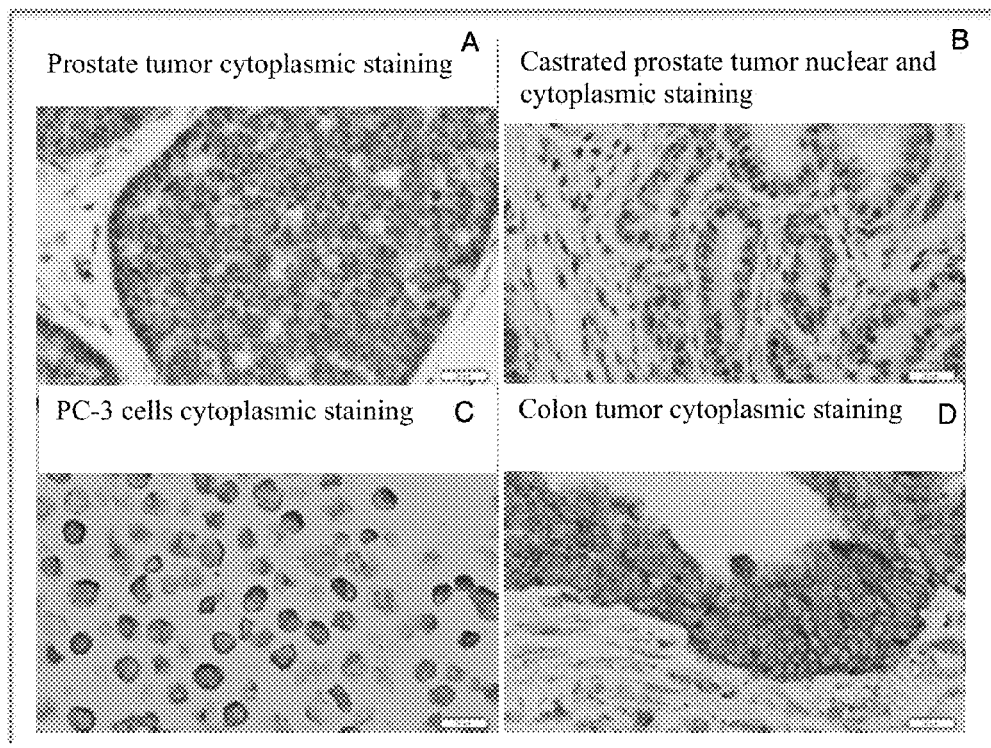
FIGS. 8A-8D. Immunohistochemical analysis of RON expression in (A) prostate tumors from (B) castrated and sham-castrated TRAMP mice. (C) Androgen independent PC-3 cells and (D) human colon tumor tissue were used as positive control. Negative controls without antibody showed no staining.

Elevated Expression of RON in Human Prostate Tumors:

Typically RON is localized to the membrane or cytoplasm. The inventors examined the expression of RON in the prostate from castrated and sham castrated transgenic adenocarcinoma of the mouse prostate (TRAMP) mice using immunohistochemistry. Interestingly the inventors found RON to be localized mostly in the nuclear compartment from castrated mice compared to sham castrated mice showing cytoplasmic and membranous localization (FIG. 8). On the other hand colon tumor showed only cytoplasmic staining.

Figure 9:
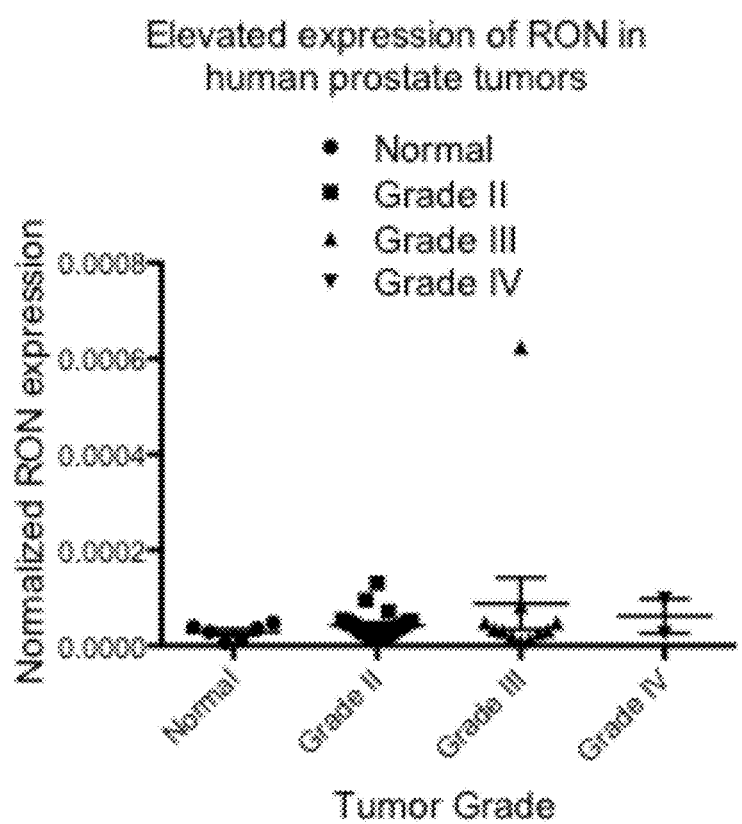
FIG. 9. Alterations in RON expression in human prostate samples. Prostate cancer cDNA array was obtained from Origene Inc. (Rockville, Md.). This tissue scan cancer array had 48 samples covering normal (n=8); state IIA (n=22): state III (n=11) and stage IV (n=2). RON expression profile was analyzed in these samples using RON specific primers and data was normalized with respect to β-actin.

The inventors investigated alterations in the expression of RON in human prostate samples using prostate cancer cDNA array (Origen USA, Rockville, Md.). This tissue scan cancer array had 48 samples covering normal (n=8); state IIA (n=22); state III (n=11) and stage IV (n=2). RON expression profile was analyzed in these samples using RON specific primers and data was normalized with respect to β-actin. As shown in FIG. 9, there is elevated expression of RON with increasing tumor grade (p=0.001) up to grade III. Grade IV did not achieve significance possibly due to small sample size. Overall these data suggest that RON expression is increased in prostate cancer and that it could play an important role during prostate carcinogenesis.

RON Expression is Upregulated in Androgen Independent Prostate Cancer Cells.

Figure 10A:
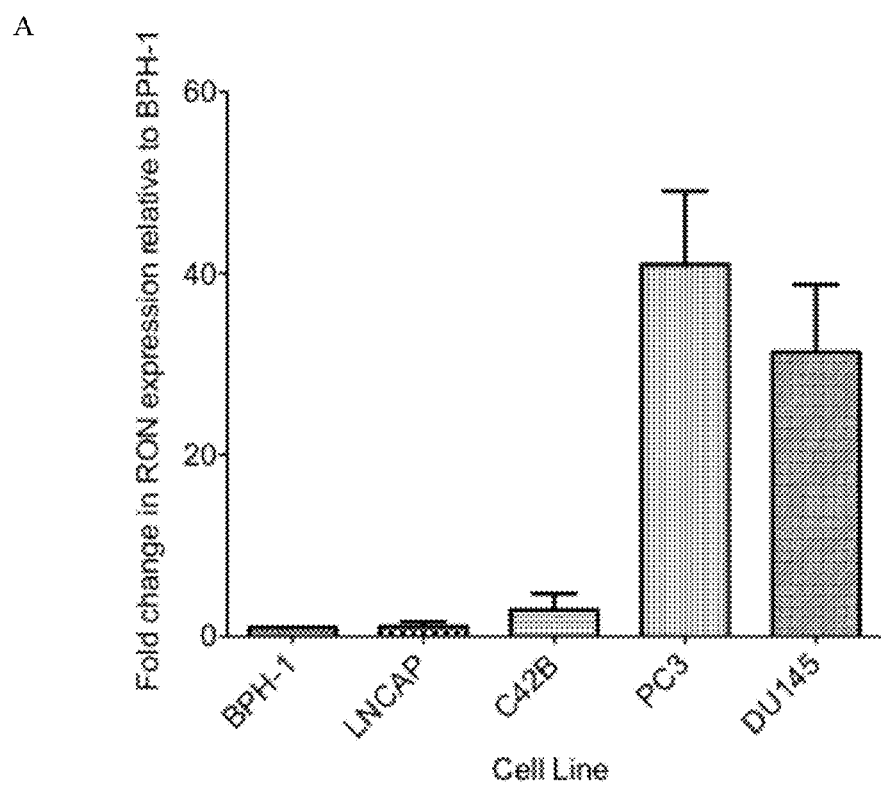
FIGS. 10A-10C. RON expression is upregulated in androgen independent prostate cancer cells. Total RNA prepared from the prostate cancer cell lines indicated in (A) was used in RT-PCR to measure levels and expression of RON. Levels of RON were normalized to β-actin levels and fold change is shown. Data presented is an average of three independent experiments. Whole cell extracts were prepared from the prostate cancer cell lines indicated in (B). The extracts were used for immunoblotting to measure levels of RON. Levels of RON were normalized to β-actin levels. The study was repeated more than three times—a representative immunoblots is shown in (B). (C) shows alterations in RON expression in human prostate samples. Prostate cancer cDNA array was obtained from Origene Inc. (Rockville, Md.). RON expression was analyzed in these samples using gene specific primers and data was normalized with respect to β-actin.
Figure 10B:
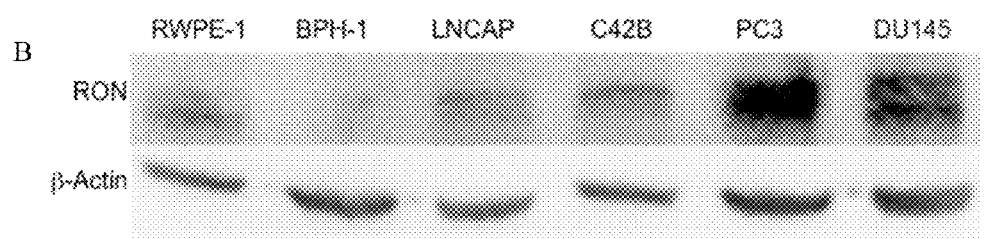
Figure 10C:
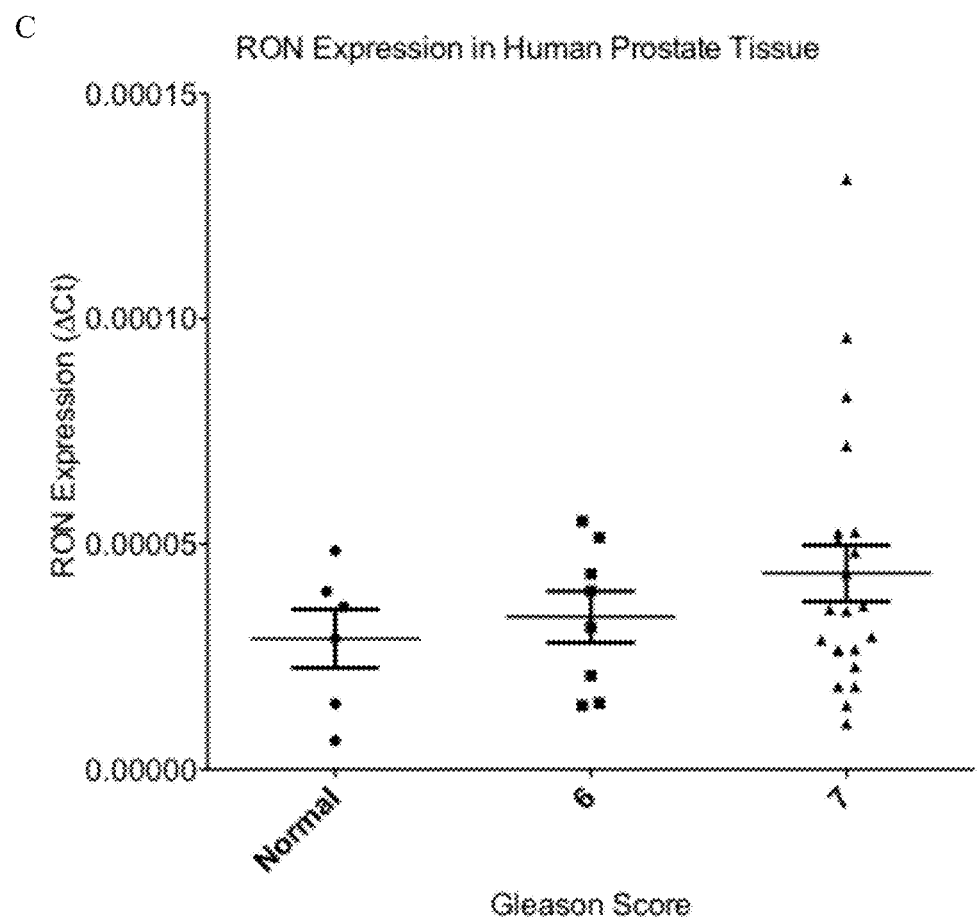

The inventors examined the protein levels and RNA expression of RON in immortalized human prostate cell line (RWPE-1) and established prostate cancer cells including androgen responsive LNCaP, androgen independent C4-2B, PC-3 and DU145. As shown in FIG. 1, endogenous expression (FIG. 10A) and levels (FIG. 10B) of RON varied among different cell lines with significantly elevated levels in androgen independent DU145 and PC-3 cells compared to non-tumorigenic BPH-1 cells. (FIG. 10A-10B) The expression of RON in human prostate tumor samples that differ in Gleason score was also examined. (FIG. 10C) The inventors observed elevated expression of RON in Gleason 7 samples indicating a potential role for RON in prostate cancer progression. Studies have reported elevated expression of anti-apoptotic protein FLIP in various tumor models. Overexpression has been reported to contribute to therapeutic resistance. The inventors have observed that FLIP expression is elevated in high-grade prostate tumors and its inhibition induces apoptosis in prostate cancer cells. Taken together these data reveal a positive correlation between RON and FLIP in prostate tumors.

RON Regulates FLIP Transcriptional Activity.

Figure 11:
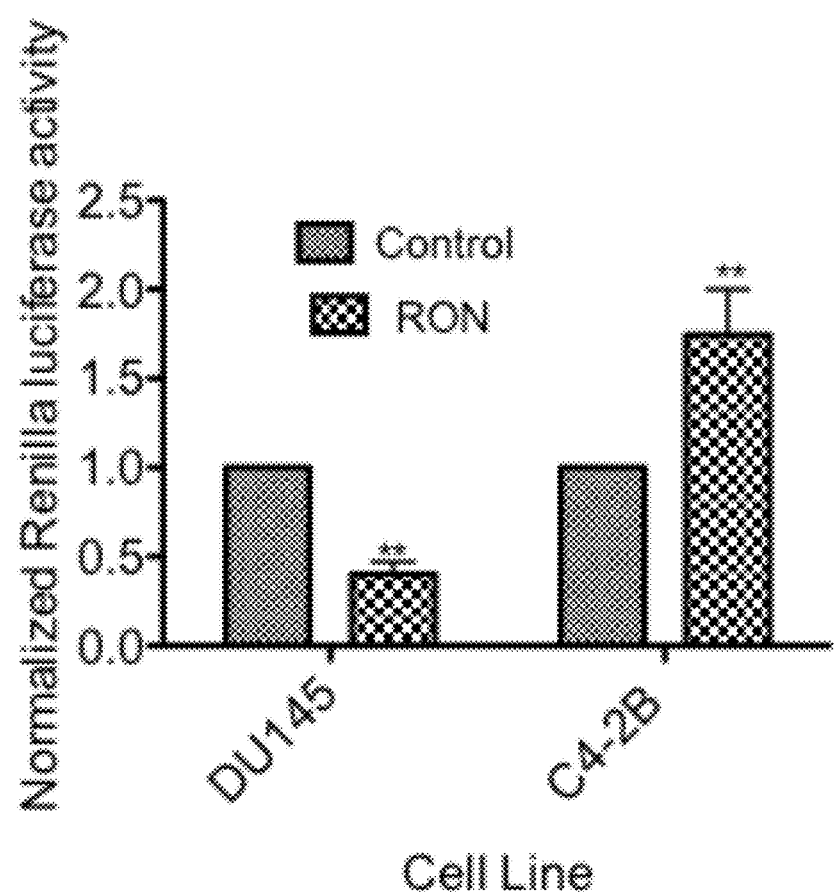
FIG. 11. Logarithmically growing androgen-independent C4-2B and DU145 cells were seeded at a density of 100,00 in 6-well plates in complete media. Following attachment (24 h after seeding) cells were co-transfected with FLIP-reporter plasmid (−121/+242) and RON expression plasmid (C4-2B) or RON siRNA (DU145) along with renilla luciferase using Lipofectamine 2000 (Life Technologies, Grand Island, N.Y.) in Opti-MEM media. Following 36 h transfection, cells were treated with 5 and 10 μg/ml Nx for 6 h. Following this incubation, cells were harvested and luciferase activity was measured using Dual-Luciferase Reporter Assay System (Promega Corp., Madison Wis.). Normalized luciferase activity with respect to pcDNA3 or scrambled control is shown. Data presented is an average of two independent experiments.
Figures 12A, 12B:
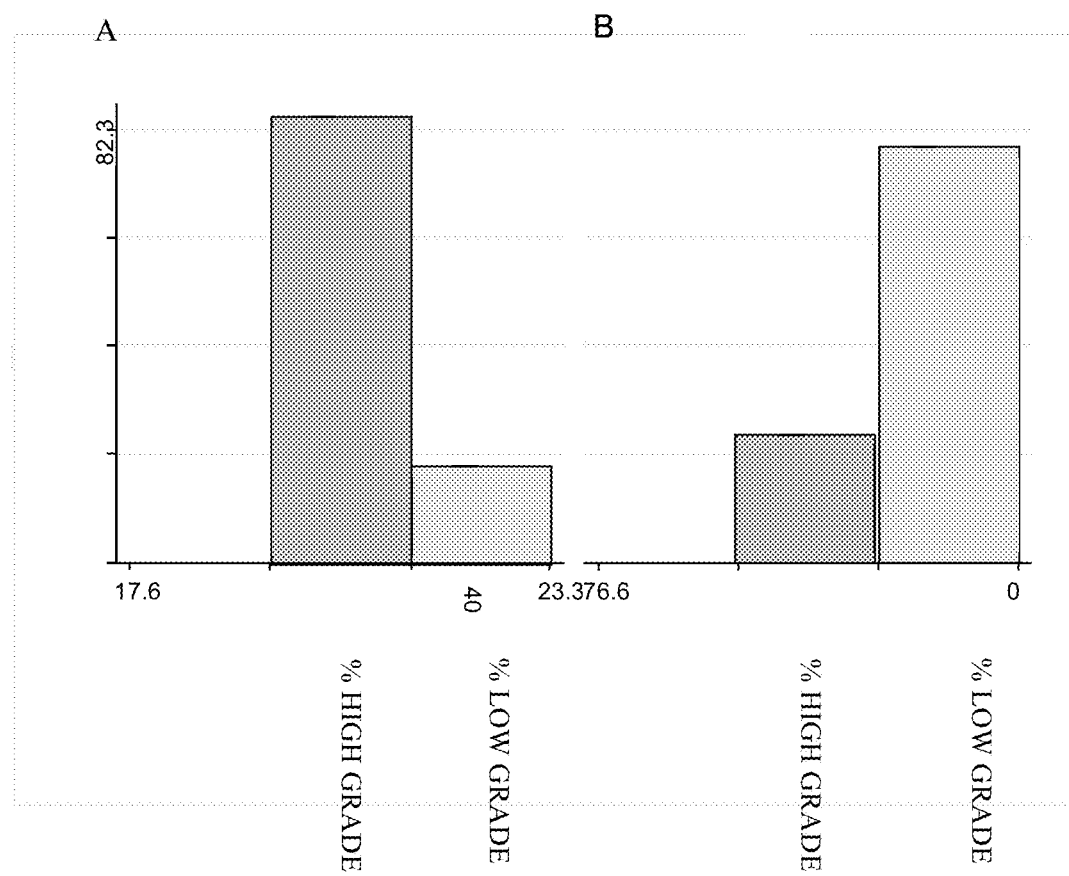
FIGS. 12A-12B. Percentage of samples showing high- or low-grade cancer between (A) recurrent and (B) non-recurrent cases as determined by pathological evaluation.

The inventors examined the effect of RON overexpression (transfecting with RON expression plasmid) in C4-2B cells (have low endogenous RON expression) or inhibiting RON expression (using siRNA) in DU145 cells (with high endogenous RON expression) on trans-activation of FLIP. These data show decreased FLIP transcriptional activity in DU145 cells with RON siRNA and increased FLIP transcriptional activity following RON overexpression in C4-2B cells (FIG. 11). These studies suggest a role for RON/FLIP axis in prostate cancer. Taken together, the experimental observations demonstrate a positive correlation between RON and FLIP in prostate carcinogenesis. Therefore adding RON to Sp1/Sp3/FLIP signature can improve (i) predictive ability of the signature panel to detect aggressive prostate tumors; and (ii) recurrence-free survival of prostate cancer patients.

Materials and Methods

Patients and Tissues:

The inventors used tissues from the GU tissue repository at The University of Texas Health Science Center, San Antonio, Tex. for which written informed consent approval was obtained from the Institutional Review Board at The University of Texas Health Science Center, San Antonio, Tex. These patients underwent radical prostatectomy as primary treatment for prostate cancer at University Hospital and the South Texas Veterans Health Care System, Audie Murphy Veterans Administration Hospital at San Antonio, Tex. Tissues used were from 64 unidentified patients (approved by the institutional review board of the University of Texas Health Science Center at San Antonio). Age range was from 51-76 years, median age 63 years (Table 1). Cases were classified as recurrent if PSA was detectable and increased to 0.2 ng/mL or higher, as confirmed by a second PSA test. Patients without recurrence had undetectable PSA levels or a PSA <0.2 ng/mL during at least a 60-month follow-up period after prostatectomy. Of the 64 subjects, 30 had recurrent cancer (47%) and 34 were without recurrence (53%). Gleason scores were significantly different between the two groups (p=0.0001): 82.35% of the non-recurrent cases (PSA non-failure) had low Gleason grade [5 to 7(3+4)], whereas 76.66% of the PSA recurrence cases (PSA failure) had high Gleason grade [7(4+3) to 9].

TABLE 1

PATIENT CHARACTERISTICS

| | Patients: 64 | Age | Non-Recurrent | Recurrent |
|---|---|---|---|---|
| Non-Recurrent: | 34, (53.13%) | Mean | 64.03 | 63.83 |
| Recurrent: | 30, (46.88%) | Median | 66 | 64.5 |
| | | Range | 52-76 | 51-76 |
| | | No significant difference between group: p = 0.82 | | |

| Grade | Gleason Non-Recurrent | Recurrent | PSA: | at Surgery | at Failure |
|---|---|---|---|---|---|
| Low grade 5-7(3 + 4) | 82.35% (28) | 23.33% (6) | Mean: Range: | 10.04 1.37-54.4 | 0.341 0.2-1 |
| High grade 7(4 + 3)-9 | 17.65% (7) | 76.66% (23) | Median: | 8.1 | 0.31 |

Antibodies and Immunohistochemistry:

Rabbit polyclonal antibodies specific for FLIP, Sp1, and Sp3 were from Santa Cruz Biotechnology (Santa Cruz, Calif.). Immunohistochemistry (IHC) was carried out in the pathology core facility of the Department of Pathology University of Texas Health Science Center at San Antonio. Staining was performed using standard IHC methods including the use of appropriate negative controls. Rabbit HRP polymer and DAB chromogen was used as the ancillary system and hematoxylin (DAKO North America Inc. Carpentaria, Calif.) was used for counterstaining.

Semiquantitative Evaluation of Tissue Staining:

Tissue sections containing 30-40% tumor were chosen for pathological evaluation. A pathologist blindly evaluated staining of prostate tissue. Staining intensities and proportion of positive staining tumor cells were determined independently. Briefly, the proportion of positive tumor cells was scored as follows: 0, no stained cells; 1, ≤1%; 2, 1-10%; 3, 10-33%; 4, 33-66%; 5, 66-100% positive staining. The intensity score (IS) represents the average staining intensity of tumor cells: 0, no staining; 1, weak; 2, moderate; 3, strong staining. The proportion score and the intensity score were added to obtain the total score (TS) with a range of 0 to 8.

Statistical Methods and Analysis:

Association of the FLIP/Sp1/Sp3 biomarker signature with clinical outcome (recurrence vs. non-recurrence) was evaluated using multiple statistical methods. The mean staining scores for expression in the two groups were compared with a Wilcoxon rank-sum test. p-values <0.05 were considered significant. The predictive value of each marker (FLIP, Sp1, and Sp3) for clinical outcome (recurrence or non recurrence) was first explored individually with logistic regression, and then the additive predicted value of the FLIP/Sp1/Sp3 signature and the extent to which they interacted with each other and with the Gleason score was explored with a backward selection model. The discrimination of the markers was identified with sensitivity-specificity analysis and the diagnostic value of the FLIP/Sp1/Sp3 signature was determined using area under the curve (AUC) for receiver operator characteristic (ROC) curves. Variables with p<0.15 were retained (Hosmer and Lemeshow (2000) Applied Logistic Regression. 2nd ed. New York, N.Y.: John Wiley & Sons, Inc.) in order to improve accuracy of the significant (p<0.05) variables reported. For the final model the Hosmer-Lemeshow Goodness of Fit test was performed. Significance levels and AUC for the ROC curve are reported. The analysis was carried out using SAS version 9.2 (SAS Institute Inc.) and STATA version 9.2 (STATA Corporation).

The invention claimed is:

1. A method for administering a prostate cancer therapy comprising
   (a) performing an assay comprising contacting a prostate sample from a subject with a detectable probe that specifically binds FLICE-inhibitory protein (FLIP) protein, a detectable probe that specifically binds transcription factor Sp1 protein, and a detectable probe that specifically binds transcription factor Sp3 protein in the prostate sample,
   (b) detecting the presence of cells having elevated levels of FLIP protein, elevated levels of transcription factor Sp1 protein, and elevated levels of transcription factor Sp3 protein in the prostate sample,
   (c) selecting the subject having prostate cells with elevated levels of FLIP protein, elevated levels of transcription factor Sp1 protein, and elevated levels of transcription factor Sp3 protein, and identifying the subject as having an increased likelihood of cancer recurrence, and (d) administering a prostate cancer treatment to the selected subject having an increased likelihood of cancer recurrence.

2. The method of claim 1, further comprising performing an assay and measuring levels of RON tyrosine kinase protein.

3. The method of claim 1, further comprising performing a Gleason score assessment of the prostate sample.

4. The method of claim 1, wherein the subject has under gone surgery to remove a cancerous lesion.

5. The method of claim 4, wherein the surgery is a prostatectomy.

6. The method of claim 3, wherein the levels of FLIP, transcription factor Sp1, and transcription factor Sp3 are determined by measuring protein levels in a prostate sample.

7. The method of claim 6, wherein the measuring of protein levels is by immuno-assay.

8. The method of claim 7, wherein the immuno-assay is immunohistochemistry.

9. The method of claim 7, wherein the immuno-assay is an enzyme linked immunoassay (ELISA).

* * * * *